(12) United States Patent
Hunter

(10) Patent No.: US 11,998,349 B2
(45) Date of Patent: Jun. 4, 2024

(54) DEVICES, SYSTEMS AND METHODS FOR MONITORING HIP REPLACEMENTS

(71) Applicant: Canary Medical Inc., Vancouver (CA)

(72) Inventor: William L. Hunter, Vancouver (CA)

(73) Assignee: Canary Medical Inc., Vancouver (CA)

( * ) Notice: Subject to any disclaimer, the term of this patent is extended or adjusted under 35 U.S.C. 154(b) by 0 days.

(21) Appl. No.: 17/383,332

(22) Filed: Jul. 22, 2021

(65) Prior Publication Data

US 2022/0015699 A1 Jan. 20, 2022

Related U.S. Application Data

(63) Continuation of application No. 14/776,650, filed as application No. PCT/US2014/028381 on Mar. 14, 2014, now abandoned.

(60) Provisional application No. 61/789,170, filed on Mar. 15, 2013.

(51) Int. Cl.
| | |
|---|---|
| *A61F 2/30* | (2006.01) |
| *A61B 5/00* | (2006.01) |
| *A61F 2/28* | (2006.01) |
| *A61F 2/32* | (2006.01) |
| *A61F 2/34* | (2006.01) |
| *A61F 2/36* | (2006.01) |
| *A61F 2/46* | (2006.01) |

(52) U.S. Cl.
CPC .......... *A61B 5/4851* (2013.01); *A61B 5/0022* (2013.01); *A61F 2/32* (2013.01); *A61F 2/34* (2013.01); *A61F 2/36* (2013.01); *A61F 2/4657* (2013.01); *A61F 2002/3067* (2013.01); *A61F 2002/4666* (2013.01); *A61F 2002/4668* (2013.01); *A61F 2002/467* (2013.01); *A61F 2002/4672* (2013.01); *A61F 2002/4674* (2013.01)

(58) Field of Classification Search
None
See application file for complete search history.

(56) References Cited

U.S. PATENT DOCUMENTS

| | | | |
|---|---|---|---|
| 4,161,782 | A | 7/1979 | McCracken |
| 4,894,728 | A | 1/1990 | Goodman |
| 5,019,794 | A | 5/1991 | Letessier et al. |
| 5,042,504 | A | 8/1991 | Huberti |
| 5,245,109 | A | 9/1993 | Kaminsky et al. |
| 5,358,202 | A | 10/1994 | Tse et al. |
| 5,383,874 | A | 1/1995 | Jackson |

(Continued)

FOREIGN PATENT DOCUMENTS

| | | |
|---|---|---|
| AT | 513434 B1 | 2/2015 |
| CA | 1212501 A | 10/1986 |

(Continued)

OTHER PUBLICATIONS

PCT International Search Report and Written Opinion dated Jul. 7, 2014, for PCT/US2014/028381.

(Continued)

*Primary Examiner* — Ann Schillinger

(57) ABSTRACT

Hip replacement prosthesis are provided, comprising a femoral stem, a femoral head coupled to the femoral stem, and an acetabular assembly coupled to the femoral head, and a plurality of sensors coupled to at least of the femoral stem, femoral head, and acetabular assembly.

25 Claims, 11 Drawing Sheets

(56) References Cited

U.S. PATENT DOCUMENTS

| | | | |
|---|---|---|---|
| 5,413,604 A | 5/1995 | Hodge | |
| 5,626,581 A | 5/1997 | Staehlin et al. | |
| 5,672,954 A | 9/1997 | Watanabe | |
| 5,716,981 A | 2/1998 | Hunter et al. | |
| 5,833,603 A | 11/1998 | Kovacs et al. | |
| H1765 H | 12/1998 | O'Phelan | |
| 5,906,643 A | 5/1999 | Walker | |
| 6,019,794 A | 2/2000 | Walker | |
| 6,206,835 B1 | 3/2001 | Spillman, Jr. et al. | |
| 6,245,109 B1 | 6/2001 | Mendes et al. | |
| 6,358,202 B1 | 3/2002 | Arent | |
| 6,374,097 B1 | 4/2002 | Kudou | |
| 6,447,448 B1* | 9/2002 | Ishikawa | A61B 5/036 600/377 |
| 6,610,096 B2* | 8/2003 | MacDonald | A61B 5/4839 623/18.11 |
| 6,610,101 B2 | 8/2003 | Herr et al. | |
| 6,620,168 B1 | 9/2003 | Lombardo et al. | |
| 6,706,071 B1* | 3/2004 | Wolter | A61F 2/32 623/22.17 |
| 6,712,778 B1 | 3/2004 | Jeffcoat et al. | |
| 6,805,667 B2 | 10/2004 | Christopherson | |
| 7,009,511 B2 | 3/2006 | Mazar et al. | |
| 7,097,662 B2 | 8/2006 | Evans, III et al. | |
| 7,127,300 B2 | 10/2006 | Mazar et al. | |
| 7,130,695 B2 | 10/2006 | Czygan et al. | |
| 7,141,026 B2 | 11/2006 | Aminian et al. | |
| 7,190,273 B2* | 3/2007 | Liao | A61B 5/4528 128/903 |
| 7,195,645 B2* | 3/2007 | Disilvestro | A61B 5/076 600/587 |
| 7,328,131 B2* | 2/2008 | Donofrio | A61F 2/4657 702/182 |
| 7,333,013 B2 | 2/2008 | Berger | |
| 7,347,874 B2* | 3/2008 | Disilvestro | A61B 5/076 600/587 |
| 7,383,071 B1 | 6/2008 | Russell et al. | |
| 7,450,332 B2 | 11/2008 | Pasolini et al. | |
| 7,463,997 B2 | 12/2008 | Pasolini et al. | |
| 7,553,923 B2 | 6/2009 | Williams et al. | |
| 7,559,951 B2* | 7/2009 | DiSilvestro | A61F 2/38 623/23.45 |
| 7,603,894 B2 | 10/2009 | Breed | |
| 7,613,497 B2* | 11/2009 | Govari | A61B 5/6846 600/407 |
| 7,813,808 B1 | 10/2010 | Doron et al. | |
| 7,819,808 B2 | 10/2010 | Oonuki | |
| 7,874,673 B2 | 1/2011 | Shinohara et al. | |
| 7,889,070 B2 | 2/2011 | Reeves | |
| 7,922,771 B2 | 4/2011 | Otto et al. | |
| 7,924,267 B2 | 4/2011 | Sirtori | |
| 8,029,566 B2 | 10/2011 | Lozier et al. | |
| 8,080,064 B2 | 12/2011 | Dietz et al. | |
| 8,109,890 B2 | 2/2012 | Kamiar et al. | |
| 8,176,922 B2 | 5/2012 | Sherman et al. | |
| 8,241,296 B2 | 8/2012 | Wasielewski | |
| 8,244,368 B2 | 8/2012 | Sherman | |
| 8,245,583 B2 | 8/2012 | Stein | |
| 8,283,793 B2 | 10/2012 | Pless | |
| 8,311,632 B2 | 11/2012 | Pless et al. | |
| 8,317,869 B2 | 11/2012 | Cloutier et al. | |
| 8,372,420 B2 | 2/2013 | Hunter et al. | |
| 8,491,569 B1 | 7/2013 | Anderson | |
| 8,551,023 B2 | 10/2013 | Sherman et al. | |
| 8,556,888 B2 | 10/2013 | Nields et al. | |
| 8,634,928 B1 | 1/2014 | O'Driscoll | |
| 8,721,643 B2 | 5/2014 | Morgan et al. | |
| 8,761,859 B2* | 6/2014 | Roche | A61B 5/1459 600/407 |
| 8,876,739 B2 | 11/2014 | Salarian et al. | |
| 8,996,892 B1 | 3/2015 | Chu et al. | |
| 9,019,098 B2 | 4/2015 | Okano | |
| 9,307,932 B2 | 4/2016 | Mariani et al. | |
| 9,364,659 B1 | 6/2016 | Rao | |
| 9,368,105 B1 | 6/2016 | Freed et al. | |
| 9,390,724 B2 | 7/2016 | List | |
| 9,393,433 B2 | 7/2016 | Parramon et al. | |
| 9,424,840 B1 | 8/2016 | Hart et al. | |
| 9,445,930 B2 | 9/2016 | Chen et al. | |
| 9,451,919 B2 | 9/2016 | Roche | |
| 9,456,915 B2 | 10/2016 | Chen et al. | |
| 9,549,742 B2 | 1/2017 | Berend et al. | |
| 9,629,583 B2 | 4/2017 | Gradel et al. | |
| 9,820,858 B2 | 11/2017 | Harris et al. | |
| 10,070,973 B2 | 9/2018 | Sherman et al. | |
| 10,219,699 B2 | 3/2019 | Wilder et al. | |
| 10,285,637 B1 | 5/2019 | Hnat et al. | |
| 10,492,686 B2 | 12/2019 | Hunter et al. | |
| 10,499,855 B2 | 12/2019 | Hunter | |
| 10,582,896 B2 | 3/2020 | Revie | |
| 10,596,009 B2 | 3/2020 | Mines et al. | |
| 11,071,279 B2 | 7/2021 | Singh et al. | |
| 11,191,479 B2 | 12/2021 | Bailey et al. | |
| 2001/0032059 A1 | 10/2001 | Kelly et al. | |
| 2001/0050087 A1 | 12/2001 | Weissman et al. | |
| 2002/0024450 A1 | 2/2002 | Townsend et al. | |
| 2002/0026224 A1 | 2/2002 | Thompson | |
| 2002/0107576 A1 | 8/2002 | Meyers et al. | |
| 2002/0113685 A1 | 8/2002 | Izaki et al. | |
| 2002/0147416 A1 | 10/2002 | Zogbi et al. | |
| 2003/0004403 A1 | 1/2003 | Drinan et al. | |
| 2003/0069644 A1 | 4/2003 | Kovacevic et al. | |
| 2003/0204267 A1 | 10/2003 | Hazebrouck et al. | |
| 2004/0011137 A1 | 1/2004 | Hnat et al. | |
| 2004/0019382 A1* | 1/2004 | Amirouche | A61B 5/4528 623/20.14 |
| 2004/0019384 A1 | 1/2004 | Kirking et al. | |
| 2004/0083003 A1 | 4/2004 | Wasielewski | |
| 2004/0113790 A1 | 6/2004 | Hamel | |
| 2004/0138757 A1* | 7/2004 | Nadzadi | A61F 2/3609 623/22.11 |
| 2004/0204635 A1 | 10/2004 | Scharf et al. | |
| 2004/0204766 A1 | 10/2004 | Siebel | |
| 2004/0211580 A1 | 10/2004 | Wang et al. | |
| 2004/0243148 A1* | 12/2004 | Wasielewski | A61B 5/062 977/932 |
| 2004/0243244 A1 | 12/2004 | Otto et al. | |
| 2004/0249464 A1 | 12/2004 | Bindseil et al. | |
| 2004/0249471 A1 | 12/2004 | Bindseil et al. | |
| 2005/0010299 A1* | 1/2005 | Disilvestro | A61B 5/1076 600/587 |
| 2005/0010301 A1* | 1/2005 | Disilvestro | A61B 5/076 623/20.14 |
| 2005/0012610 A1 | 1/2005 | Liao et al. | |
| 2005/0021126 A1 | 1/2005 | Machan et al. | |
| 2005/0027192 A1 | 2/2005 | Govari et al. | |
| 2005/0065408 A1 | 3/2005 | Benderev | |
| 2005/0165317 A1 | 7/2005 | Turner et al. | |
| 2005/0171594 A1 | 8/2005 | Machan et al. | |
| 2005/0181005 A1 | 8/2005 | Hunter et al. | |
| 2005/0181009 A1 | 8/2005 | Hunter et al. | |
| 2005/0228410 A1 | 10/2005 | Berreklouw | |
| 2005/0242666 A1 | 11/2005 | Huscher et al. | |
| 2005/0245992 A1 | 11/2005 | Persen et al. | |
| 2005/0288563 A1 | 12/2005 | Feliss et al. | |
| 2006/0009856 A1 | 1/2006 | Sherman et al. | |
| 2006/0030771 A1 | 2/2006 | Levine et al. | |
| 2006/0030945 A1 | 2/2006 | Wright | |
| 2006/0036246 A1 | 2/2006 | Carl et al. | |
| 2006/0047283 A1 | 3/2006 | Evans, III et al. | |
| 2006/0069403 A1 | 3/2006 | Shalon et al. | |
| 2006/0111777 A1 | 5/2006 | Chen | |
| 2006/0116744 A1 | 6/2006 | Von et al. | |
| 2006/0142670 A1 | 6/2006 | DiSilvestro et al. | |
| 2006/0152377 A1 | 7/2006 | Beebe et al. | |
| 2006/0165317 A1 | 7/2006 | Gzybowski | |
| 2006/0184067 A1 | 8/2006 | Clark et al. | |
| 2006/0224088 A1 | 10/2006 | Roche | |
| 2006/0229711 A1 | 10/2006 | Yan et al. | |
| 2006/0229730 A1 | 10/2006 | Railey et al. | |
| 2006/0271112 A1 | 11/2006 | Martinson | |
| 2006/0271199 A1* | 11/2006 | Johnson | A61F 2/4657 600/431 |

(56) References Cited

U.S. PATENT DOCUMENTS

| | | |
|---|---|---|
| 2006/0282168 A1 | 12/2006 | Sherman et al. |
| 2007/0004994 A1 | 1/2007 | Sherman |
| 2007/0005141 A1 | 1/2007 | Sherman |
| 2007/0034013 A1 | 2/2007 | Moon et al. |
| 2007/0060955 A1 | 3/2007 | Strother et al. |
| 2007/0067018 A1 | 3/2007 | Miller |
| 2007/0088442 A1* | 4/2007 | Cima ............... A61B 5/4528 600/431 |
| 2007/0089518 A1 | 4/2007 | Ericson et al. |
| 2007/0126696 A1 | 6/2007 | Boillot |
| 2007/0151884 A1 | 7/2007 | Black |
| 2007/0161884 A1 | 7/2007 | Black et al. |
| 2007/0167809 A1 | 7/2007 | Dala-Krishna |
| 2007/0179628 A1 | 8/2007 | Rochetin |
| 2007/0179739 A1 | 8/2007 | Donofrio et al. |
| 2007/0211022 A1 | 9/2007 | Boillot |
| 2007/0211023 A1 | 9/2007 | Boillot |
| 2007/0233065 A1 | 10/2007 | Donofrio et al. |
| 2007/0233267 A1 | 10/2007 | Amirouche et al. |
| 2007/0234819 A1 | 10/2007 | Amirouche et al. |
| 2007/0238984 A1 | 10/2007 | Maschke et al. |
| 2007/0238992 A1* | 10/2007 | Donofrio ............... A61B 8/56 600/437 |
| 2007/0239282 A1 | 10/2007 | Caylor et al. |
| 2007/0265662 A1 | 11/2007 | Ufford |
| 2007/0288194 A1 | 12/2007 | Boillot |
| 2008/0020012 A1 | 1/2008 | Ju et al. |
| 2008/0027679 A1 | 1/2008 | Shklarski |
| 2008/0033527 A1 | 2/2008 | Nunez et al. |
| 2008/0048878 A1 | 2/2008 | Boillot |
| 2008/0065225 A1 | 3/2008 | Wasielewski et al. |
| 2008/0076972 A1 | 3/2008 | Dorogusker et al. |
| 2008/0088436 A1 | 4/2008 | Reeves et al. |
| 2008/0114270 A1 | 5/2008 | DiSilvestro et al. |
| 2008/0139954 A1 | 6/2008 | Day et al. |
| 2008/0214903 A1 | 9/2008 | Orbach |
| 2008/0215609 A1 | 9/2008 | Cleveland et al. |
| 2008/0235621 A1 | 9/2008 | Boillot |
| 2008/0275350 A1 | 11/2008 | Liao et al. |
| 2008/0300597 A1 | 12/2008 | Morgan et al. |
| 2008/0300659 A1 | 12/2008 | Matos |
| 2008/0306325 A1 | 12/2008 | Burnett et al. |
| 2008/0309481 A1 | 12/2008 | Tanaka et al. |
| 2009/0005708 A1 | 1/2009 | Johanson et al. |
| 2009/0005876 A1 | 1/2009 | Dietz et al. |
| 2009/0012372 A1 | 1/2009 | Burnett et al. |
| 2009/0048524 A1 | 2/2009 | Wildau et al. |
| 2009/0076358 A1 | 3/2009 | Reggiardo et al. |
| 2009/0088756 A1 | 4/2009 | Anderson |
| 2009/0099570 A1* | 4/2009 | Paradis ............... A61B 34/20 128/898 |
| 2009/0119222 A1 | 5/2009 | O'Neil |
| 2009/0149964 A1 | 6/2009 | May et al. |
| 2009/0157146 A1 | 6/2009 | Linder et al. |
| 2009/0192533 A1 | 7/2009 | Dlugos, Jr. et al. |
| 2009/0253587 A1 | 10/2009 | Fernandez |
| 2009/0264894 A1 | 10/2009 | Wasielewski |
| 2009/0299228 A1 | 12/2009 | Lozier et al. |
| 2010/0014626 A1 | 1/2010 | Fennell et al. |
| 2010/0057046 A1 | 3/2010 | Stevens et al. |
| 2010/0100011 A1* | 4/2010 | Roche ............... A61B 5/4528 623/20.14 |
| 2010/0145337 A1 | 6/2010 | Janna et al. |
| 2010/0152621 A1 | 6/2010 | Janna et al. |
| 2010/0164705 A1 | 7/2010 | Blanchard |
| 2010/0191100 A1 | 7/2010 | Anderson et al. |
| 2010/0204551 A1 | 8/2010 | Roche |
| 2010/0204802 A1* | 8/2010 | Wilson ............... A61B 5/24 623/23.6 |
| 2010/0204955 A1 | 8/2010 | Roche et al. |
| 2010/0249533 A1 | 9/2010 | Pierce et al. |
| 2010/0249787 A1 | 9/2010 | Roche |
| 2010/0249790 A1 | 9/2010 | Roche |
| 2010/0250284 A1 | 9/2010 | Roche et al. |
| 2010/0262160 A1 | 10/2010 | Boyden et al. |
| 2010/0285082 A1 | 11/2010 | Fernandez |
| 2010/0287422 A1 | 11/2010 | Miyazaki |
| 2010/0312188 A1 | 12/2010 | Robertson et al. |
| 2010/0326187 A1 | 12/2010 | Stein |
| 2010/0326194 A1 | 12/2010 | Stein et al. |
| 2010/0326210 A1 | 12/2010 | Stein et al. |
| 2010/0326211 A1 | 12/2010 | Stein |
| 2010/0327848 A1 | 12/2010 | Stein |
| 2010/0327880 A1 | 12/2010 | Stein |
| 2010/0328077 A1 | 12/2010 | Stein |
| 2010/0328098 A1 | 12/2010 | Stein et al. |
| 2010/0331663 A1 | 12/2010 | Stein |
| 2010/0331679 A1 | 12/2010 | Stein |
| 2010/0331680 A1 | 12/2010 | Stein |
| 2010/0331681 A1 | 12/2010 | Stein et al. |
| 2010/0331682 A1 | 12/2010 | Stein et al. |
| 2010/0331685 A1 | 12/2010 | Stein et al. |
| 2010/0331687 A1 | 12/2010 | Stein et al. |
| 2010/0331704 A1 | 12/2010 | Stein et al. |
| 2010/0331718 A1 | 12/2010 | Stein |
| 2010/0331733 A1 | 12/2010 | Stein |
| 2010/0331734 A1 | 12/2010 | Stein |
| 2010/0331738 A1 | 12/2010 | Stein et al. |
| 2010/0331894 A1 | 12/2010 | Stein |
| 2010/0331932 A1 | 12/2010 | Stevenson et al. |
| 2010/0332152 A1 | 12/2010 | Stein |
| 2011/0004076 A1 | 1/2011 | Janna et al. |
| 2011/0015693 A1 | 1/2011 | Williamson |
| 2011/0019595 A1 | 1/2011 | Magar et al. |
| 2011/0054272 A1 | 3/2011 | Derchak |
| 2011/0060220 A1 | 3/2011 | Roche et al. |
| 2011/0063094 A1 | 3/2011 | Meiertoberens et al. |
| 2011/0077736 A1 | 3/2011 | Rofougaran |
| 2011/0077865 A1 | 3/2011 | Chen et al. |
| 2011/0087306 A1 | 4/2011 | Goossen |
| 2011/0092860 A1 | 4/2011 | Salarian et al. |
| 2011/0092948 A1 | 4/2011 | Shachar et al. |
| 2011/0098576 A1 | 4/2011 | Hollstien |
| 2011/0158206 A1 | 6/2011 | Shrestha et al. |
| 2011/0160572 A1 | 6/2011 | McIntosh et al. |
| 2011/0160583 A1 | 6/2011 | Roche et al. |
| 2011/0160616 A1 | 6/2011 | Stein et al. |
| 2011/0184740 A1 | 7/2011 | Gruenstein et al. |
| 2011/0196501 A1 | 8/2011 | Michelson |
| 2011/0200052 A1 | 8/2011 | Mungo et al. |
| 2011/0213221 A1 | 9/2011 | Roche |
| 2011/0213413 A1 | 9/2011 | Brown et al. |
| 2011/0224564 A1 | 9/2011 | Moon et al. |
| 2011/0288436 A1 | 11/2011 | Stone |
| 2011/0288805 A1 | 11/2011 | Dejnabadi et al. |
| 2011/0319755 A1 | 12/2011 | Stein et al. |
| 2012/0029326 A1 | 2/2012 | Raptis et al. |
| 2012/0035868 A1 | 2/2012 | Roche et al. |
| 2012/0095526 A1 | 4/2012 | Roche |
| 2012/0116310 A1 | 5/2012 | Forsell |
| 2012/0123498 A1 | 5/2012 | Gross |
| 2012/0123716 A1 | 5/2012 | Clark |
| 2012/0130687 A1 | 5/2012 | Otto et al. |
| 2012/0152017 A1 | 6/2012 | Stein et al. |
| 2012/0157839 A1 | 6/2012 | Stein |
| 2012/0157884 A1 | 6/2012 | Stein et al. |
| 2012/0166680 A1 | 6/2012 | Masoud et al. |
| 2012/0190940 A1 | 7/2012 | Stein |
| 2012/0191206 A1 | 7/2012 | Stein et al. |
| 2012/0216611 A1 | 8/2012 | Stein et al. |
| 2012/0220839 A1 | 8/2012 | Stein et al. |
| 2012/0226360 A1 | 9/2012 | Stein et al. |
| 2012/0226364 A1 | 9/2012 | Kampas et al. |
| 2012/0232834 A1 | 9/2012 | Roche et al. |
| 2012/0283600 A1 | 11/2012 | Stein |
| 2012/0313760 A1 | 12/2012 | Okano |
| 2012/0323333 A1 | 12/2012 | Metzger |
| 2012/0330367 A1 | 12/2012 | Roche et al. |
| 2013/0011008 A1 | 1/2013 | Kezoye et al. |
| 2013/0023794 A1 | 1/2013 | Stein et al. |
| 2013/0023795 A1 | 1/2013 | Stein et al. |
| 2013/0027186 A1 | 1/2013 | Cinbis et al. |
| 2013/0079668 A1 | 3/2013 | Stein et al. |

(56) References Cited

U.S. PATENT DOCUMENTS

| | | | |
|---|---|---|---|
| 2013/0079669 A1 | 3/2013 | Stein et al. | |
| 2013/0079670 A1 | 3/2013 | Stein et al. | |
| 2013/0079671 A1 | 3/2013 | Stein et al. | |
| 2013/0079672 A1 | 3/2013 | Stein et al. | |
| 2013/0079674 A1 | 3/2013 | Stein et al. | |
| 2013/0079675 A1 | 3/2013 | Stein et al. | |
| 2013/0079679 A1 | 3/2013 | Roche et al. | |
| 2013/0079790 A1 | 3/2013 | Stein et al. | |
| 2013/0079884 A1 | 3/2013 | Stein et al. | |
| 2013/0109998 A1 | 5/2013 | Swoboda et al. | |
| 2013/0110008 A1 | 5/2013 | Bourget et al. | |
| 2013/0123684 A1 | 5/2013 | Giuffrida et al. | |
| 2013/0144379 A1 | 6/2013 | Najafi et al. | |
| 2013/0179110 A1 | 7/2013 | Lee | |
| 2013/0197656 A1* | 8/2013 | Conrad | A61F 2/32 623/22.11 |
| 2013/0215979 A1 | 8/2013 | Yakovlev et al. | |
| 2013/0225949 A1 | 8/2013 | Roche | |
| 2013/0225982 A1 | 8/2013 | McIntosh et al. | |
| 2013/0226034 A1 | 8/2013 | Stein et al. | |
| 2013/0226035 A1 | 8/2013 | Stein et al. | |
| 2013/0252610 A1 | 9/2013 | Kim et al. | |
| 2013/0261450 A1 | 10/2013 | Stein et al. | |
| 2013/0268081 A1* | 10/2013 | Stein | A61B 5/6846 623/18.11 |
| 2013/0281839 A1 | 10/2013 | Yan et al. | |
| 2013/0317367 A1 | 11/2013 | Shuler | |
| 2013/0325019 A1 | 12/2013 | Thomas et al. | |
| 2013/0338455 A1 | 12/2013 | Gradel et al. | |
| 2013/0338770 A1 | 12/2013 | Boyden et al. | |
| 2014/0009262 A1 | 1/2014 | Robertson et al. | |
| 2014/0025338 A1 | 1/2014 | Blount et al. | |
| 2014/0031063 A1 | 1/2014 | Park et al. | |
| 2014/0058289 A1 | 2/2014 | Panken et al. | |
| 2014/0085102 A1 | 3/2014 | McCormick | |
| 2014/0094715 A1 | 4/2014 | Stein et al. | |
| 2014/0107796 A1 | 4/2014 | Stein et al. | |
| 2014/0135589 A1 | 5/2014 | Osorio | |
| 2014/0135616 A1 | 5/2014 | Stein et al. | |
| 2014/0135624 A1 | 5/2014 | Stein et al. | |
| 2014/0135655 A1 | 5/2014 | Stein et al. | |
| 2014/0135773 A1 | 5/2014 | Stein et al. | |
| 2014/0136143 A1 | 5/2014 | Stein et al. | |
| 2014/0148676 A1 | 5/2014 | Stein et al. | |
| 2014/0163645 A1 | 6/2014 | Dinsmoor et al. | |
| 2014/0171754 A1 | 6/2014 | Stein et al. | |
| 2014/0180697 A1 | 6/2014 | Torok et al. | |
| 2014/0188007 A1 | 7/2014 | Stein et al. | |
| 2014/0194707 A1 | 7/2014 | Stein et al. | |
| 2014/0200584 A1 | 7/2014 | Stein et al. | |
| 2014/0213867 A1 | 7/2014 | Pletcher et al. | |
| 2014/0256324 A1 | 9/2014 | Mohanty et al. | |
| 2014/0257047 A1 | 9/2014 | Sillay et al. | |
| 2014/0275815 A1 | 9/2014 | Stein et al. | |
| 2014/0275849 A1 | 9/2014 | Acquista | |
| 2014/0275861 A1 | 9/2014 | Kroh et al. | |
| 2014/0276240 A1 | 9/2014 | Stein et al. | |
| 2014/0276241 A1 | 9/2014 | Stein et al. | |
| 2014/0276885 A1 | 9/2014 | Stein et al. | |
| 2014/0276887 A1 | 9/2014 | Stein et al. | |
| 2014/0277542 A1 | 9/2014 | Stein et al. | |
| 2014/0288464 A1 | 9/2014 | Stein | |
| 2014/0296663 A1 | 10/2014 | Boyden et al. | |
| 2014/0303739 A1 | 10/2014 | Mentink et al. | |
| 2014/0322935 A1 | 10/2014 | Filman et al. | |
| 2014/0328253 A1 | 11/2014 | Lee et al. | |
| 2014/0330105 A1 | 11/2014 | Roche | |
| 2014/0378872 A1 | 12/2014 | Hong et al. | |
| 2015/0032215 A1 | 1/2015 | Slamin et al. | |
| 2015/0032217 A1 | 1/2015 | Bojarski et al. | |
| 2015/0039093 A1 | 2/2015 | McTighe et al. | |
| 2015/0057775 A1 | 2/2015 | Dong | |
| 2015/0080901 A1 | 3/2015 | Stein | |
| 2015/0088253 A1 | 3/2015 | Doll et al. | |
| 2015/0124675 A1 | 5/2015 | Farmer et al. | |
| 2015/0164401 A1 | 6/2015 | Toth et al. | |
| 2015/0202494 A1 | 7/2015 | Hollenbach et al. | |
| 2015/0238304 A1 | 8/2015 | Lamraoui | |
| 2015/0238691 A1 | 8/2015 | Boyden et al. | |
| 2015/0335290 A1 | 11/2015 | Hunter | |
| 2016/0025978 A1 | 1/2016 | Mallinson | |
| 2016/0029952 A1 | 2/2016 | Hunter | |
| 2016/0029998 A1 | 2/2016 | Brister et al. | |
| 2016/0038087 A1 | 2/2016 | Hunter | |
| 2016/0051823 A1 | 2/2016 | Maile et al. | |
| 2016/0081762 A1 | 3/2016 | Stein et al. | |
| 2016/0101281 A1 | 4/2016 | Chen | |
| 2016/0106533 A1 | 4/2016 | Galstian et al. | |
| 2016/0128573 A1 | 5/2016 | Wilder et al. | |
| 2016/0166201 A1 | 6/2016 | Stein et al. | |
| 2016/0192878 A1 | 7/2016 | Hunter | |
| 2016/0199658 A1 | 7/2016 | Nassif et al. | |
| 2016/0232322 A1 | 8/2016 | Mensinger et al. | |
| 2016/0302721 A1 | 10/2016 | Wiedenhoefer et al. | |
| 2016/0310077 A1* | 10/2016 | Hunter | A61B 5/6862 |
| 2016/0338644 A1 | 11/2016 | Connor | |
| 2016/0340177 A1 | 11/2016 | Takada | |
| 2016/0374566 A1 | 12/2016 | Fung et al. | |
| 2017/0035593 A1 | 2/2017 | Chen et al. | |
| 2017/0049963 A1 | 2/2017 | Varsavsky et al. | |
| 2017/0119316 A1 | 5/2017 | Herrmann et al. | |
| 2017/0119472 A1 | 5/2017 | Herrmann et al. | |
| 2017/0119566 A1 | 5/2017 | Chen et al. | |
| 2017/0138986 A1 | 5/2017 | Kern | |
| 2017/0156288 A1 | 6/2017 | Singh | |
| 2017/0156632 A1 | 6/2017 | Swiston et al. | |
| 2017/0181825 A1 | 6/2017 | Hunter | |
| 2017/0189553 A1 | 7/2017 | Hunter | |
| 2017/0196478 A1 | 7/2017 | Hunter | |
| 2017/0196499 A1 | 7/2017 | Hunter | |
| 2017/0196507 A1 | 7/2017 | Singh et al. | |
| 2017/0196508 A1 | 7/2017 | Hunter | |
| 2017/0196509 A1 | 7/2017 | Hunter | |
| 2017/0252187 A1 | 9/2017 | Chapman et al. | |
| 2017/0294949 A1 | 10/2017 | Zhang et al. | |
| 2017/0328931 A1 | 11/2017 | Zhang et al. | |
| 2017/0333080 A1 | 11/2017 | Roschak et al. | |
| 2018/0000380 A1 | 1/2018 | Stein et al. | |
| 2018/0028824 A1 | 2/2018 | Pivonka et al. | |
| 2018/0055443 A1 | 3/2018 | Stein et al. | |
| 2018/0064335 A1 | 3/2018 | Rutschman et al. | |
| 2018/0125365 A1 | 5/2018 | Hunter et al. | |
| 2018/0177607 A1 | 6/2018 | Trabish et al. | |
| 2018/0177611 A1 | 6/2018 | Trabish et al. | |
| 2018/0177612 A1 | 6/2018 | Trabish et al. | |
| 2018/0228428 A1 | 8/2018 | Anker et al. | |
| 2018/0235546 A1 | 8/2018 | Hunter | |
| 2019/0038361 A1 | 2/2019 | Wasielewski | |
| 2019/0038425 A1 | 2/2019 | Otto et al. | |
| 2019/0076033 A1 | 3/2019 | Sweeney et al. | |
| 2019/0076273 A1 | 3/2019 | Goodchild et al. | |
| 2019/0192072 A1 | 6/2019 | Bailey et al. | |
| 2019/0231555 A1 | 8/2019 | Neubardt | |
| 2019/0247197 A1 | 8/2019 | Jagannathan et al. | |
| 2019/0290451 A1 | 9/2019 | Trabish et al. | |
| 2019/0350518 A1 | 11/2019 | Bailey et al. | |
| 2019/0350519 A1 | 11/2019 | Bailey et al. | |
| 2019/0350520 A1 | 11/2019 | Bailey et al. | |
| 2019/0350521 A1 | 11/2019 | Bailey et al. | |
| 2019/0350522 A1 | 11/2019 | Bailey et al. | |
| 2019/0350523 A1 | 11/2019 | Bailey et al. | |
| 2020/0054215 A1 | 2/2020 | Roche | |
| 2020/0093430 A1 | 3/2020 | Bailey et al. | |
| 2020/0093431 A1 | 3/2020 | Bailey et al. | |
| 2020/0155327 A1 | 5/2020 | Suh et al. | |
| 2021/0077241 A1 | 3/2021 | Hunter | |

FOREIGN PATENT DOCUMENTS

| | | |
|---|---|---|
| CA | 2620247 A1 | 3/2007 |
| CA | 3017932 A1 | 9/2017 |
| CN | 1806776 A | 7/2006 |
| CN | 1899222 A | 1/2007 |
| CN | 101060815 A | 10/2007 |

(56) References Cited

FOREIGN PATENT DOCUMENTS

| | | |
|---|---|---|
| CN | 101254103 A | 9/2008 |
| CN | 101257860 A | 9/2008 |
| CN | 101273925 A | 10/2008 |
| CN | 101296673 A | 10/2008 |
| CN | 101426453 A | 5/2009 |
| CN | 101484085 A | 7/2009 |
| CN | 101495025 A | 7/2009 |
| CN | 101536938 A | 9/2009 |
| CN | 101573085 A | 11/2009 |
| CN | 101773387 | 7/2010 |
| CN | 101849865 A | 10/2010 |
| CN | 202036215 | 11/2011 |
| CN | 101773387 B | 12/2011 |
| CN | 102688097 A | 9/2012 |
| CN | 102740803 A | 10/2012 |
| CN | 102885626 A | 1/2013 |
| CN | 102905649 A | 1/2013 |
| CN | 103313661 A | 9/2013 |
| CN | 103458830 A | 12/2013 |
| CN | 103735303 A | 4/2014 |
| CN | 103957992 A | 7/2014 |
| CN | 105283150 A | 1/2016 |
| CN | 2580920 Y | 3/2018 |
| CN | 109310324 A | 2/2019 |
| DE | 4322619 C1 | 9/1994 |
| DE | 19924676 A1 | 11/2000 |
| DE | 10342823 A1 | 4/2005 |
| EP | 1528902 B1 | 11/2006 |
| EP | 2018825 | 1/2009 |
| EP | 1814471 | 3/2010 |
| EP | 2967879 B1 | 1/2022 |
| EP | 2967879 B1 * | 1/2022 | ........... A61B 5/0022 |
| IN | 101287408 A | 10/2008 |
| JP | 2001046411 A | 2/2001 |
| JP | 2003527926 A | 9/2003 |
| JP | 2005520630 A | 7/2005 |
| JP | 2005288172 A | 10/2005 |
| JP | 2006055629 A | 3/2006 |
| JP | 2006102498 A | 4/2006 |
| JP | 2007083019 A | 4/2007 |
| JP | 2007535372 A | 12/2007 |
| JP | 2008501488 A | 1/2008 |
| JP | 2008510584 A | 4/2008 |
| JP | 2011514812 A | 5/2011 |
| JP | 2013039444 A | 2/2013 |
| JP | 2016525389 A | 8/2016 |
| JP | 2017023436 A | 2/2017 |
| JP | 2017510307 A | 4/2017 |
| JP | 2022128381 A | 9/2022 |
| KR | 101274641 B1 | 6/2013 |
| KR | 20140133419 A | 11/2014 |
| WO | 1997033513 A1 | 9/1997 |
| WO | 02064019 A2 | 8/2002 |
| WO | 2004016204 A1 | 2/2004 |
| WO | 2004091419 A2 | 10/2004 |
| WO | 2005120203 A2 | 12/2005 |
| WO | 2006089069 | 8/2006 |
| WO | 2006105098 A2 | 10/2006 |
| WO | 2006108065 A2 | 10/2006 |
| WO | 2006113394 A2 | 10/2006 |
| WO | 2008032316 A2 | 3/2008 |
| WO | 2008035089 A1 | 3/2008 |
| WO | 2008103181 A1 | 8/2008 |
| WO | 2008152549 A2 | 12/2008 |
| WO | 2009145633 A1 | 12/2009 |
| WO | 2009148847 A2 | 12/2009 |
| WO | 2010111678 A2 | 9/2010 |
| WO | 2012006066 A1 | 1/2012 |
| WO | 2012061825 A2 | 5/2012 |
| WO | 2012095784 A1 | 7/2012 |
| WO | 2012103549 A1 | 8/2012 |
| WO | 2013022890 A1 | 2/2013 |
| WO | 2013044117 A1 | 3/2013 |
| WO | 2013044127 A1 | 3/2013 |
| WO | 2013044157 A1 | 3/2013 |
| WO | 2013044160 A2 | 3/2013 |
| WO | 2013044165 A2 | 3/2013 |
| WO | 2013044174 A2 | 3/2013 |
| WO | 2014053956 A1 | 4/2014 |
| WO | 2014100795 A1 | 6/2014 |
| WO | 2014144070 A1 | 9/2014 |
| WO | 2014144107 A1 | 9/2014 |
| WO | 2014144707 A1 | 9/2014 |
| WO | 2014209916 A1 | 12/2014 |
| WO | 2015021807 A1 | 2/2015 |
| WO | 2015038979 A1 | 3/2015 |
| WO | 2015188867 A1 | 12/2015 |
| WO | 2015200704 A1 | 12/2015 |
| WO | 2015200707 A1 | 12/2015 |
| WO | 2015200718 A1 | 12/2015 |
| WO | 2015200720 A2 | 12/2015 |
| WO | 2015200722 A2 | 12/2015 |
| WO | 2015200723 A1 | 12/2015 |
| WO | 2016044651 A1 | 3/2016 |
| WO | 2016065205 A1 | 4/2016 |
| WO | 2016174612 A1 | 11/2016 |
| WO | 2016180653 A1 | 11/2016 |
| WO | 2016180654 A1 | 11/2016 |
| WO | 2017152153 A1 | 9/2017 |
| WO | 2017165717 A1 | 9/2017 |
| WO | 2018119360 A1 | 6/2018 |

OTHER PUBLICATIONS

PCT International Search Report and Written Opinion dated Oct. 15, 2014, for PCT/US2014/043736.
PCT International Search Report and Written Opinion dated Feb. 1, 2016, for PCT/US2015/050789.
PCT International Search Report and Written Opinion dated Aug. 2, 2017, for PCT/US2017/023916.
PCT International Search Report and Written Opinion dated Oct. 30, 2020, for PCT/US2020/036516.
European Extended Search Report dated Mar. 17, 2017, for 14762650.1.
European Partial Search Report dated Jun. 13, 2017, for 14817351.9.
European Partial Search Report dated Oct. 16, 2018 for 15842678.3.
European Full Extended Search Report dated Nov. 12, 2018 for 15812631.8.
European Extended Search Report dated Feb. 5, 2019 for 15842678.3.
Arami, Arash et al., "Instrumented Prosthesis for Knee Implant Monitoring", 2011 IEEE International Conference on Automation Science and Engineering, Trieste, Italy, Aug. 24-27, 2011, pp. 828-835.
Arami, Arash et al., "Accurate Measurement of Concurrent Flexion-Extension and Internal-External Rotations in Smart Knee Prostheses", IEEE Transactions on BioMedical Engineering, v. 60, No. 9, Sep. 2013, pp. 2504-2510.
Bosch Sensortec Data Sheet for BMI160 Small, low power inertial measurement unit, Doc Rev 0.8, Release Date Feb. 10, 2015, No. BST-BMI160-DS000-07, 110 pp.
Bosch for BMI160 Small, low power inertial measurement unit, Jan. 15, 2015, 2 pp.
Bosch Press Release, "Bosch Sensortec launches first IMU with sub 1mA current consumption", Jun. 25, 2014, 3 pp.
Ebrahim, A. F., et al., "The use of fiber Bragg grating sensors in biomechanics and rehabilitation applications: The state-of-the-art and ongoing research topics", Sensors, 2012, v 12, No. 10, pp. 12890-12929 OSCH Press Release, "Bosch Sensortec launches first IMU with sub 1mA current consumption", Jun. 25, 2014, 3 pp.
Forchelet, David et al. "Enclosed Electronic System for Force Measurements in Knee Implants", Sensors 2014, vol. 14, pp. 15009-15021.
Graichen, F., et al., "Hip endoprosthesis for in vivo measurement of joint force and termperative", Journal of Biomechanics, 1999, v 32, No. 10, pp. 1113-1117.
Heinlein, Bernd et al., "Design, calibration and pre-clinical testing of an instrumented tibial tray", Journal of Biomechanics, vol. 40, 2007, pp. S4-S10.

(56) References Cited

OTHER PUBLICATIONS

Jacq, Caroline et al., "Investigation of Polymer Thick-Film Piezoresistors for Medical Wrist Rehabilitation and Artificial Knee Load Sensors", Procedia Engineering, vol. 87, 2014, pp. 1194-1197.
Kroft, Steve, "The Data Brokers: Selling your Personal Information" pp. 1-8, extracted from Google on Sep. 4, 2014 is a script from "The Data Brokers" aired on Mar. 9, 2014 on 60 Minutes CBS.
Park, Min-Ho, MD et al., "Using a Tibial Short Extension Stem Reduces Tibial Component Loosening After Primary Total Knee Arthroplasty in Severely Varus Knees: Long-term Survival Analysis with Propensity Score Matching," The Journal of Arthroplasty, vol. 33, 2018, pp. 2512-2517.
Ries, Michael D., "Endosteal Referencing in Revision Total Knee Arthroplasty," The Journal of Arthroplasty, vol. 13, No. 1, pp. 85-91. (1998).
Simoncini, Matteo; "Design and integration of an instrumented knee prosthesis", Thesis No. 6379 (2014), École Polytechnique Fédérale de Lausanne.
Zimmer® NexGen® RH Knee Brochure 8 pp.
Almouahed S., et al., "New Trends in Instrumented Knee Prostheses," International Conference on Information and Communication Technologies: From Theory to Applications, Apr. 7-11, 2008, 6 Pages.
Angers-Goulet M., et al., "Up to Seven Years' Follow-up of Short Cemented Stems in Complex Primary Total Knee Arthroplasty: a Prospective Study," The Knee, Accepted on May 13, 2017, vol. 24, pp. 1166-1174.
Chandrakasan A.P., et al., "Next Generation Micro-Power Systems," Symposium on VLSI Circuits Digest of Technical Papers, 2008, pp. 1-5, 04 pages.
Christian R., MD., et al., "Short-keeled Cemented Tibial Components Show an Increased Risk for Aseptic Loosening," Clinical Orthopaedics and Related Research, Mar. 2013, vol. 471, No. 3, pp. 1008-1013.
Cushner F., MD., et al., "Feasibility and Compliance of Monitoring Post-Operative Activity Levels in TKA Patients Using Wireless Technology," Lenox Hill Hospital, Northwell Health, PPT Presentation, 1 Page.
D'Apuzzo M.R., et al., "Morbid Obesity Independently Impacts Complications, Mortality, and Resource Use After TKA," Clinical Orthopaedics and Related Research, Jan. 2015, Published Online on May 13, 2014, vol. 473, No. 01, pp. 57-63.
Extended European Search Report for European Application No. 14762269.0, mailed Oct. 24, 2016, 08 Pages.
Extended European Search Report for European Application No. 14762650.1, mailed Jul. 21, 2017, 10 Pages.
Extended European Search Report for European Application No. 17771204.9, mailed Feb. 28, 2020, 09 Pages.
Extended European Search Report for European Application No. 20214094.3, mailed May 28, 2021, 07 Pages.
Extended European Search Report for European Application No. 22153300.3, mailed Jul. 18, 2022, 07 Pages.
International Preliminary Report on Patentability for International Application No. PCT/US2014/028381, mailed Sep. 24, 2015, 13 Pages.
International Preliminary Report on Patentability for International Application No. PCT/US2014/043736, mailed Jan. 7, 2016, 11 Pages.
International Preliminary Report on Patentability for International Application No. PCT/US2015/050789, mailed Mar. 30, 2017, 07 Pages.
International Preliminary Report on Patentability for International Application No. PCT/US2017/023916, mailed Oct. 4, 2018, 20 Pages.
International Preliminary Report on Patentability for International Application No. PCT/US2020/036516, mailed Dec. 16, 2021, 10 Pages.
Loh N.C., et al., "Sub-10 cm3 Interferometric Accelerometer with Nano-g Resolution," Journal of Microelectromechanical Systems, vol. 11, No. 3, Jun. 2002, pp. 182-187.
Malin A.S., MD., et al., "Routine Surveillance of Modular PFC TKA Shows Increasing Failures after 10 Years," Clinical Orthopaedics and Related Research, Sep. 2010, vol. 468, No. 9, pp. 2469-2476.
Old A.B., et al., "Revision of Total Knee Arthroplasties Performed in Young, Active Patients with Posttraumatic Arthritis and Osteoarthritis," J. Knee Surg, Nov. 2017, vol. 30, No. 9, pp. 905-908, 1 Page.
Parratte S., MD., et al., "Do Stemmed Tibial Components in Total Knee Arthroplasty Improve Outcomes in Patients with Obesity?," Clinical Orthopaedics and Related Research, Jan. 2017, vol. 475, No. 1, pp. 137-145.
Partial Supplementary European Search Report for European Application No. 14762650.1, mailed Apr. 13, 2017, 08 Pages.
Partial Supplementary European Search Report for European Application No. 14817352.9, mailed Feb. 14, 2017, 09 Pages.
Patil S., MD., et al., "How Do Knee Implants Perform Past the Second Decade? Nineteen- to 25-year Followup of he Press-fit Condylar Design TKA," Clinical Orthopaedics and Related Research, Jan. 2015, vol. 473, No. 1, pp. 135-140.
Polla D.L., et al., "Microdevices in Medicine," Annual Review Of Biomedical Engineering, 2000, vol. 02, pp. 551-576.
Singh U.K., et al., "Piezoelectric Power Scavenging of Mechanical Vibration Energy," Australian Mining Technology Conference, Oct. 2-4, 2007, pp. 111-118.
Xiang X., et al., "A Review of the Implantable Electronic Devices in Biology and Medicine," China Academic Journal Electronic Publishing House, vol. 32 (3), Mar. 3, 2004, pp. 462-467.
Xie, Xiang et al., "A Review of the Implantable Electronic Devices in Biology and Medicine", ACTA Electronica Sinica, vol. 32, No. 3, Mar. 2004, pp. 462-467.
Yeh R., et al., "Single Mask, Large Force, and Large Displacement Electrostatic Linear Inchworm Motors," Journal of Microelectromechanical Systems, Aug. 4, 2002, vol. 11, No. 4, pp. 330-336, XP011064780.
Yiming L., et al., "Application of Wireless Sensor Networks in Healthcare," Chinese Journal of Medical Instrumentation, Dec. 31, 2013, vol. 37, No. 5, pp. 351-354.
Yiming L., et al., "Application of Wireless Sensor Networks in Healthcare," Chinese Journal of Medical Instrumentation, vol. 37 (5), Dec. 31, 2013, pp. 351-354 and Figure 1.
Yoon C., MD., et al., "Medial Tibial Periprosthetic Bone Resorption and Its Effect on Clinical Outcomes after Total Knee Arthroplasty: Cobalt-Chromium versus Titanium Implants," The Journal of Arthroplasty, Accepted Manuscript on Apr. 16, 2018, 43 Pages.
Yun K-S., et al., "A Surface-Tension Driven Micropump for Low-voltage and Low-Power Operations", Journal of Microelectromechanical Systems, Oct. 5, 2002, vol. 11, No. 5, pp. 454-461, DOI:10.1109/JMEMS.2002.803286, XP001192816.
Zimmer: "Persona The Personalized Knee Systems," Brochure, 2014, 12 Pages.
European Search Report in European Patent Application No. 23177756.6, dated Nov. 8, 2023, 8 Pages.
Laqua D., "Intelligent Power Management Enables Autonomous Power Supply of Sensor Systems for Modern Prostheses", Journal of Biomedical Engineering / Biomedizinische Technik, Published by Walter de Gruyter, Sep. 6, 2012, vol. 57, Supp. 1, pp. 247-250.

\* cited by examiner

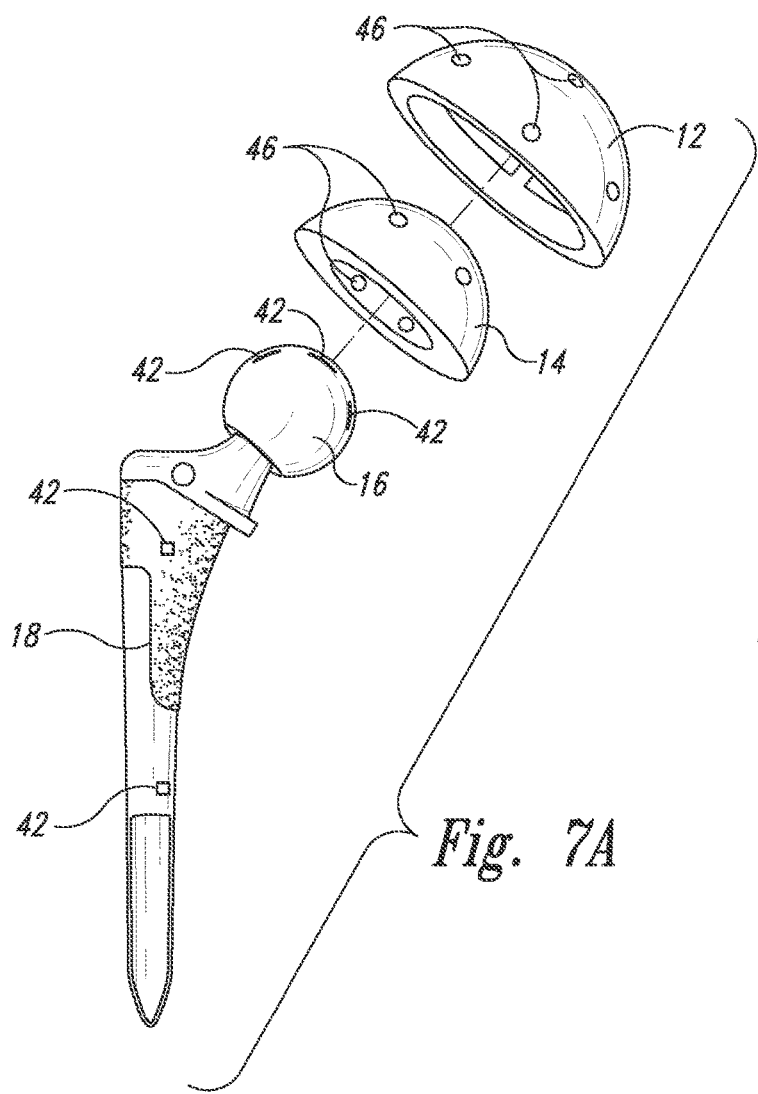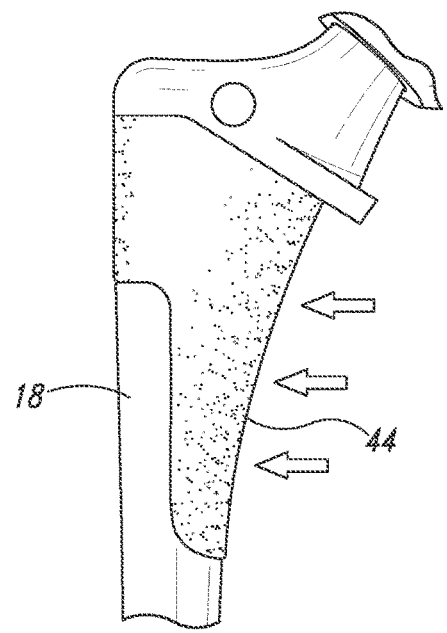
Fig. 7A
Fig. 7B
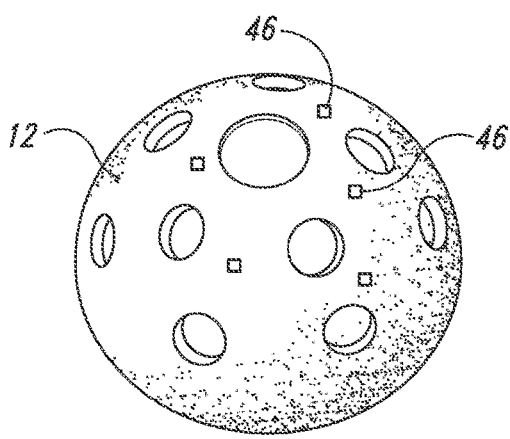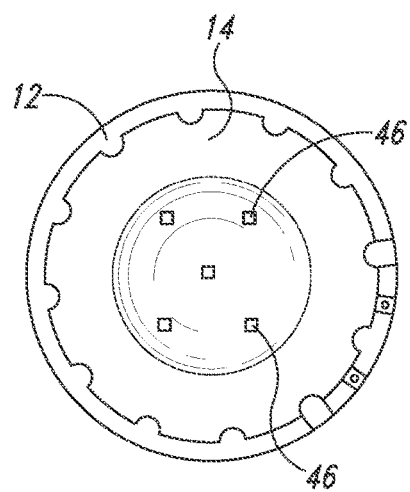
Fig. 8A
Fig. 8B

DEVICES, SYSTEMS AND METHODS FOR MONITORING HIP REPLACEMENTS

CROSS-REFERENCE TO RELATED APPLICATION

This application is a Continuation of U.S. application Ser. No. 14/776,650 filed Sep. 14, 2015, which is a national phase application under 35 U.S.C. § 371 of International Application No. PCT/US2014/028381, filed Mar. 14, 2014, which claims the benefit under 35 U.S.C. § 119(e) of U.S. Provisional Patent Application No. 61/789,170 filed Mar. 15, 2013, which applications are incorporated herein by reference in their entireties for all purposes.

FIELD OF THE INVENTION

The present invention relates generally to hip replacements, and more specifically, to devices and methods for monitoring the performance of total and partial hip replacements.

BACKGROUND

Description of the Related Art

Hip replacement is one of the most common orthopedic surgical procedures. It may be carried out when the patient loses sufficient use of the hip, typically due to injury, avascular necrosis of the hip, or for the treatment of extreme and/or constant joint pain (e.g., due to various types of arthritis (such as rheumatoid or osteoarthritis)).

Hip replacement can take a variety of different forms. In total hip replacement (THR), both the femoral head and the acetabulum are replaced. In a hemi (partial) hip arthroplasty, only the femoral head is replaced while the patient's own acetabulum is retained. The femoral component of a hip replacement may be a single piece with the head and stem as an integral, complete unit, or it may be constructed in several pieces, such as a femoral stem which is then coupled to a separate femoral head piece and neck section (which is often done to provide the patient with custom fitting for length and/or femoral head size). The femoral component can be cemented in place with a bone cement (cemented hip) or it can be fitted precisely within the medullary canal of the femur and held in place without cement (AML—anatomic medullary locking—stem design). Similarly, the acetabular component of a THR can also be a single piece coupled to the hip socket to receives the femoral head, or be a two-piece component with a shell coupled to the pelvic bone and an inner liner attached to the shell. The acetabular component of a THR can be held in place with screws and/or cement or it can be affixed without cement.

Currently, the various components may be made of the same material (e.g., all portions can be made of metal), or individual components can be made from a variety of different materials. For example, it is common for the acetabular component to have a metal shell with an outer surface coating to facilitate bone attachment and ingrowth, and an inner lining made from polyethylene, ultrahigh molecular weight polyethylene, ceramic, or surgical-grade stainless steel. Similarly, there may be several different combinations of materials used in the construction of the femoral head. For example, the femoral head can be composed of metal, usually cobalt chromium (but also stainless steel or titanium), or a ceramic material, while the femoral stem is typically metal (stainless steel, titanium, or cobalt chromium) and often possesses a surface coating to encourage incorporation of the implant within the femur.

FIG. 1 shows a total hip joint of a type known in the art. FIG. 2 is an exploded view of the total hip joint of FIG. 1. The acetabular shell may be made of any suitable material, preferably a metal or ceramic, and the inner liner may also be made of any suitable material that is compatible with the material for the acetabular shell. For example, the liner may be made of a polyethylene, an ultrahigh molecular weight polyethylene, a ceramic, a metal, or other types of material. The femoral head may be made of a metal or a ceramic and can be of the same, or different, material from that which composes the acetabular liner; for example, a ceramic femoral head on a ceramic acetabular liner (ceramic-on-ceramic hip; COC), a metal femoral head on a metal acetabulum (metal-on-metal hip; MOM) or alternatively a metal or ceramic femoral head on a polyethylene acetabular liner (metal-on-polyurethane, MOP; metal-on-cross-linked-polyurethane, MOXP; ceramic-on-polyurethane, COP; ceramic-on-cross-linked-polyurethane, COXP), or other combinations of the like. The femoral stem is usually made of a metal (stainless steel, titanium, cobalt chromium) that is biocompatible for long-term use in the patient and is inserted into the shaft of the femur and held in place with, or without, bone cement.

Unfortunately, when a total hip is inserted, various complications may arise over time. For example, as shown in FIG. 3, there may be wear between the femoral head and the acetabular liner, which leads to improper operation of the artificial hip joint. In addition, the patient may experience inflammation and pain if there is slight movement or dislocation of any of the components. Depending on the types of materials used for the acetabular liner (if present, as in THR) and the femoral head (both THR and Hemi-arthroplasty), there may be wear in the acetabular liner and/or the femoral head which results in loosening or partial (or full) dislocation of the joint, may degrade the performance of the hip, result in difficulty in movement and ambulation, and may cause pain and inflammation for the patient. A second common complication occurs when, over a period of time (for example 8-12 years), bone loss occurs in the tissues surrounding the implant in either the pelvis and/or the femur due to a process known as osteolysis.

Erosion of the bone around the implant may be caused by material debris (metal, ceramic, and/or polyurethane fragments) generated by friction between the femoral head and acetabular cup entering the tissues surrounding the implant and causing inflammation and bone loss. Other potential causes of inflammation and osteolysis are implant vibration and motion, mechanical wear and tear, lack of biocompatibility between the implant materials and the surrounding bone, metal allergy, and lack of biocompatibility between the bone cement and the surrounding bone. Additional complications include infection, nerve damage, material sensitivity, nerve impingement, and hip dislocation (more likely to occur if the muscle has not sufficiently healed; usually during the first 4-12 weeks post-surgery).

Currently, post-operative, in-hospital monitoring of hip replacement surgery patients is conducted through personal visits by the hospital staff and medical team, physical examination of the patient, medical monitoring (vital signs, etc.), evaluation of hip range of motion (ROM), physiotherapy (including early mobilization and activity), and diagnostic imaging studies and blood work as required. Once the patient is discharged from hospital, prosthesis performance and patient satisfaction is checked during periodic doctor's office visits where a thorough history, physical exam and supplemental imaging and diagnostic studies are used to monitor patient progress and identify the development of any potential complications. During such visits, the surgeon typically evaluates the range of motion of the hip, attempts to identify any pain that occurs during certain motions or actions, and questions the patient to determine activity levels, daily functioning, pain control, and rehabilitation progress.

Unfortunately, most of the patient's recuperative period occurs between hospital or office visits. It can, therefore, be very difficult to accurately measure and follow full joint range of motion (ROM can change depending on pain control, degree of anti-inflammatory medication, time of day, recent activities, and/or how the patient is feeling at the time of the examination), "real life" prosthesis performance, patient activity levels, exercise tolerance, and the effectiveness of rehabilitation efforts (physiotherapy, medications, etc.) from the day of surgery through to full recovery. For much of this information, the physician is dependent upon patient self-reporting or third party observation to obtain insight into post-operative treatment effectiveness and recovery and rehabilitation progress; in many cases this is further complicated by a patient who is uncertain what to look for, has no knowledge of what "normal/expected" post-operative recovery should be, is non-compliant, or is unable to effectively communicate their symptoms. Furthermore, identifying and tracking complications (in and out of hospital) prior to them becoming symptomatic, arising between doctor visits, or those whose presence is difficult to detect would also provide beneficial, additional information to the management of THR patients. Currently, in all instances, neither the physician nor the patient has access to the type of "real time," continuous, objective, prosthesis performance measurements that they might otherwise like to have.

The present invention discloses novel total and partial hip replacements which overcome many of the difficulties of previous hip prostheses, methods for constructing and monitoring these novel hip replacements, and further provides other related advantages.

SUMMARY

Briefly stated, full and partial hip prostheses are provided with a number of sensors to monitor the integrity and efficaciousness of the artificial hip joint within the patient. The sensors may be positioned on the outer surface of the prosthetic hip, on the inner surfaces of the prosthetic hip, within the prosthetic material (stainless steel, titanium, cobalt chromium, polyurethane, high molecular weight polyurethane, ceramics, etc.) itself, between the various components that comprise the prosthetic hip, within the bone cement (e.g., PMMA, or PMMA and MMA copolymer blends) used to secure the hip (if present), and/or within the tissues surrounding the prosthesis. Within certain embodiments, the sensors are of the type that are passive and thus do not require their own power supply.

Within one aspect of the invention assemblies are provided for positioning and placement within a patient an implant comprising a total or partial hip prosthesis; and a sensor positioned on, in, or around the prosthesis. Within various embodiments the sensor can be positioned on an outer surface of the prosthetic hip, on an inner surface of the prosthetic hip, within the materials used to construct the prosthetic hip, between the various components that make up the prosthetic hip, on or in the bone cement used to secure the prosthetic hip, on or in the tissues surrounding the prosthetic hip (typically bone or bone marrow, but also muscle, ligament, tendon, joint capsule and/or synovial compartment), or any combination of these. Representative examples of sensors suitable for use within the present invention include accelerometers (acceleration, tilt, vibration, shock and rotation sensors), pressure sensors, contact sensors, position sensors, chemical microsensors, tissue metabolic sensors, mechanical stress sensors and temperature sensors. Within particularly preferred embodiments the sensor is a wireless sensor, or a sensor connected to a wireless microprocessor.

Within further embodiments a plurality of the aforementioned sensors are positioned on, within, or around (bone cement or tissue) the prosthetic hip, and within preferred embodiments, the prosthetic hip can contain more than one type of sensor (e.g., one or more of, or any combination of the following: acceleration sensors, tilt sensors, vibration sensors, shock sensors, rotation sensors, pressure sensors, contact sensors, position sensors, chemical microsensors, tissue metabolic sensors, and mechanical stress sensors).

According to various embodiments, sensors are placed at different locations in a replacement hip joint in order to monitor the operation, movement, function, wear, performance, potential side effects and medical status of the artificial hip and its interface with the live tissue of the patient. Live, continuous, in situ, monitoring of patient activity, patient function, prosthesis activity, prosthesis function, prosthesis performance, and potential side effects is provided. In addition, information is available on many aspects of the hip replacement prosthesis and its interaction with the patient's own body tissues, including clinically important measurements not currently available through physical examination, medical imaging and diagnostic medical studies.

According to one embodiment the sensors provide evaluation data on the range of motion (ROM) of the hip. Currently, ROM is usually measured clinically by the physician passively moving the hip joint through a full range of motion during physical examination and recording the results (degrees of flexion, extension, abduction, adduction, external rotation, internal rotation and rotation in flexion). Motion sensors and accelerometers can be used to accurately determine the full ROM of the prosthetic hip joint both during physical examination and during normal daily activities between visits.

According to one embodiment, contact sensors are provided between the prosthesis and the surrounding bone, between the prosthesis and the surrounding bone cement, and/or between the bone cement and the surrounding bone in order to measure bone erosion and loosening around the implant. In other embodiments, strain gauges are provided to detect the strain between the prosthesis and the surrounding bone, between the prosthesis and the surrounding bone cement, between the bone cement and the surrounding bone, and also the strain which is exerted on the various portions of the prosthesis. Sudden increases in strain may indicate that too much stress is being placed on the replacement prosthesis, which may increase damage to the body. For example, a gradual, long-term decrease in strain may cause bone reabsorption around the implant, leading to loosening of the prosthesis or fractures in the bone surrounding the prosthesis.

According to other embodiments, accelerometers are provided which detect vibration, shock, tilt and rotation. According to other embodiments, sensors for measuring surface wear, such as contact or pressure sensors, may be embedded at different depths within the femoral head, the acetabulum, and/or the acetabular cup in order to monitor articular surface erosion. In other embodiments, position sensors, as well as other types of sensors, are provided which indicate the range of motion and monitor for partial (or complete) hip dislocation in actual use over a period of time.

Within further embodiments, the artificial hip (total or partial) can contain sensors at specified densities in specific locations. For example, the artificial hip can have a density of sensors of greater than one, two, three, four, five, six, seven, eight, nine, or ten sensors (e.g., acceleration sensors, tilt sensors, vibration sensors, shock sensors, rotation sensors, pressure sensors, contact sensors, position sensors, chemical microsensors, tissue metabolic sensors, and mechanical stress sensors, or any combination of these) per square centimeter of the device. Within other embodiments, the artificial hip (total or partial) can have a density of sensors of greater than one, two, three, four, five, six, seven, eight, nine, or ten sensors (e.g., acceleration sensors, tilt sensors, vibration sensors, shock sensors, rotation sensors, pressure sensors, contact sensors, position sensors, chemical microsensors, tissue metabolic sensors, and mechanical stress sensors, or any combination of these) per cubic centimeter of the device. Within related embodiments, the sensors (e.g., acceleration sensors, tilt sensors, vibration sensors, shock sensors, rotation sensors, pressure sensors, contact sensors, position sensors, chemical microsensors, tissue metabolic sensors, and mechanical stress sensors) can be positioned at particular locations on, within, or around the artificial hip, including for example, the femoral stem, the femoral neck, the femoral head, the acetabular cup, the acetabular lining, within portions of the device which are to be connected (e.g., the connecting segments of the femoral stem, femoral neck and femoral head; the connecting segments of the acetabular cup and the acetabular lining), and around the artificial hip (on or in the bone cement used to secure the prosthetic hip, on or in the tissues surrounding the prosthetic hip—typically bone or bone marrow, but also muscle, ligament, tendon, joint capsule and/or synovial compartment).

Within certain embodiments of the invention, the total or partial hip prosthesis is provided with a specific unique identifying number, and within further embodiments, each of the sensors on, in or around the prosthetic hip each have either a specific unique identification number, or a group identification number (e.g., an identification number that identifies the sensor as an acceleration sensor, a tilt sensor, a vibration sensor, a shock sensor, a rotation sensor, a pressure sensor, a contact sensor, a position sensor, a chemical microsensor, a tissue metabolic sensor, or a mechanical stress sensor). Within yet further embodiments, the specific unique identification number or group identification number is specifically associated with a position on, in or around the prosthetic hip.

Within other aspects of the invention methods are provided for monitoring an implanted total or partial hip prosthesis comprising the steps of transmitting a wireless electrical signal from a location outside the body to a location inside the body; receiving the signal at a sensor positioned on, in or around an artificial hip located inside the body; powering the sensor using the received signal; sensing data at the sensor; and outputting the sensed data from the sensor to a receiving unit located outside of the body.

The integrity of the partial or total hip prosthesis can be wirelessly interrogated and the results reported on a regular basis. This permits the health of the patient to be checked on a regular basis or at any time as desired by the patient and/or physician.

Within further embodiments, each of the sensors contains a signal-receiving circuit and a signal output circuit. The signal-receiving circuit receives an interrogation signal that includes both power and data collection request components. Using the power from the interrogation signal, the sensor powers up the parts of the circuitry needed to conduct the sensing, carries out the sensing, and then outputs the data to the interrogation module. The interrogation module acts under control of a control unit which contains the appropriate I/O circuitry, memory, a controller in the form of a microprocessor, and other circuitry in order to drive the interrogation module. Within yet other embodiments the sensor (e.g., an acceleration sensor, a tilt sensor, a vibration sensor, a shock sensor, a rotation sensor, a pressure sensor, a contact sensor, a position sensor, a chemical microsensor, a tissue metabolic sensor, or a mechanical stress sensor) are constructed such that they may readily be incorporated into or otherwise mechanically attached to the hip prosthesis (e.g., by way of a an opening or other appendage that provides permanent attachment of the sensor to the hip prosthesis) and/or readily incorporated into the bone cement or the tissues that surround the hip prosthesis.

Within yet other aspects of the invention methods devices are provided suitable for transmitting a wireless electrical signal from a location outside the body to a location inside the body; receiving the signal at one of the aforementioned sensors positioned on, in or around a prosthetic hip located inside the body; powering the sensor using the received signal; sensing data at the sensor; and outputting the sensed data from the sensor to a receiving unit located outside of the body. Within certain embodiments the receiving unit can provide an analysis of the signal provided by the sensor.

The data collected by the sensors can be stored in a memory located within the femoral stem. During a visit to the physician, the data can be downloaded via a wireless sensor, and the doctor is able to obtain data representative of real-time performance of the prosthesis.

The advantages obtained include more accurate monitoring of the prosthesis and permitting medical reporting of accurate, in situ, data that will contribute to the health of the patient. The details of one or more embodiments are set forth in the description below. Other features, objects and advantages will be apparent from the description, the drawings, and the claims. In addition, the disclosures of all patents and patent applications referenced herein are incorporated by reference in their entirety.

BRIEF DESCRIPTION OF THE DRAWINGS

FIG. 7A is a side view of the femoral implant with the ball attached.

FIG. 7B is an enlarged side view of the femoral implant with various sensors and a power generation segment.

FIG. 8A is a top side view of an acetabular cup having various sensors according to the embodiments described herein.

FIG. 8B is a liner in the acetabular cup of FIG. 9 having various sensors therein.

DETAILED DESCRIPTION OF THE INVENTION

Figure 1:
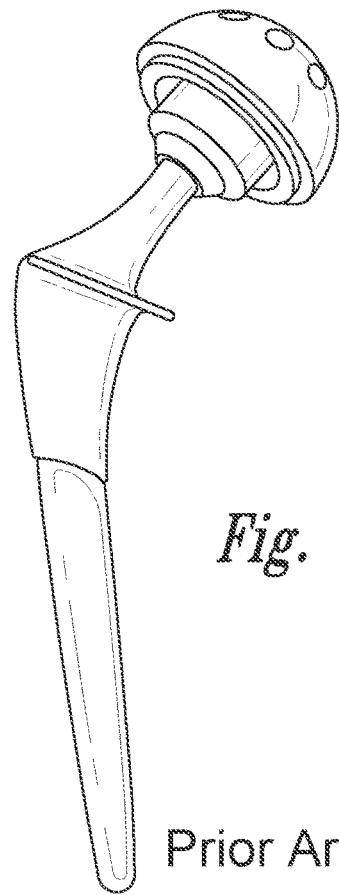
FIG. 1 is an isometric view of a total hip replacement.
Figure 2:
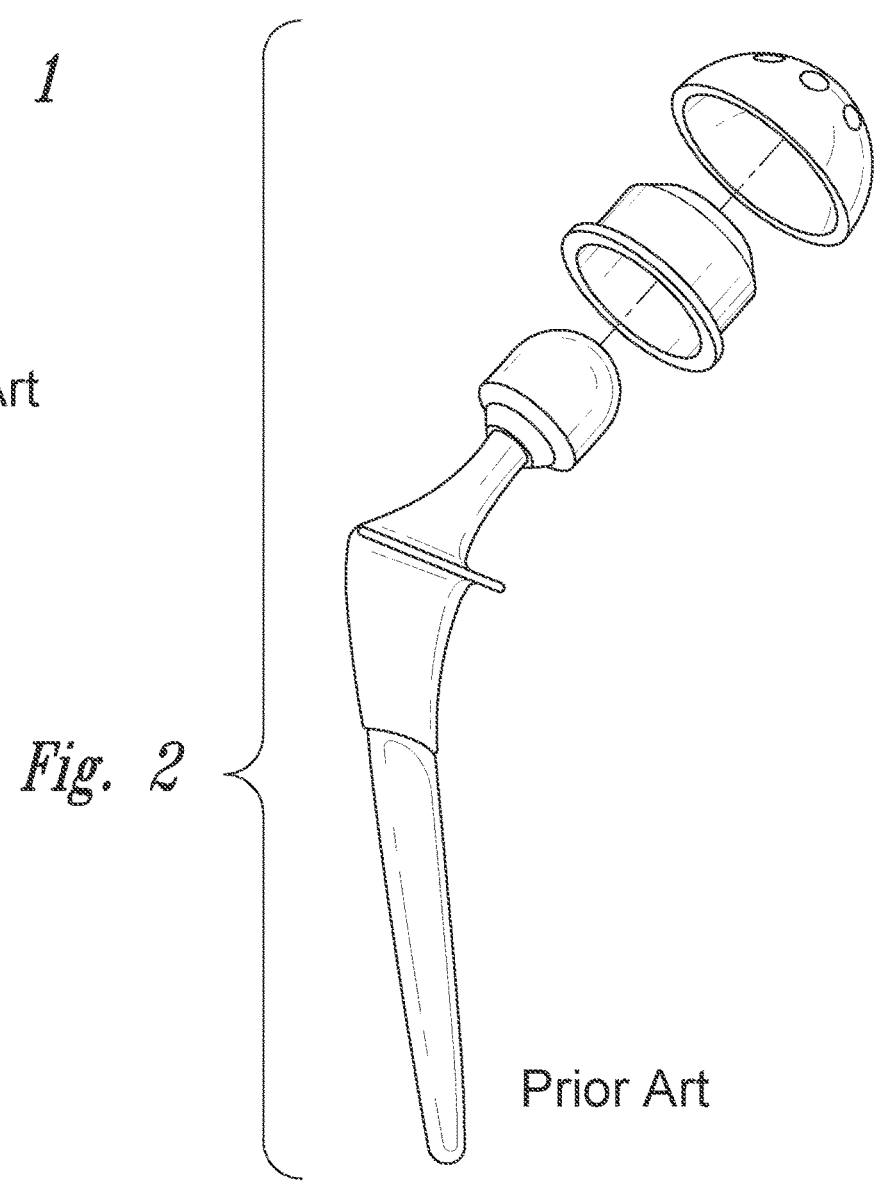
FIG. 2 is an exploded view of the total hip replacement of FIG. 1.
Figure 3:
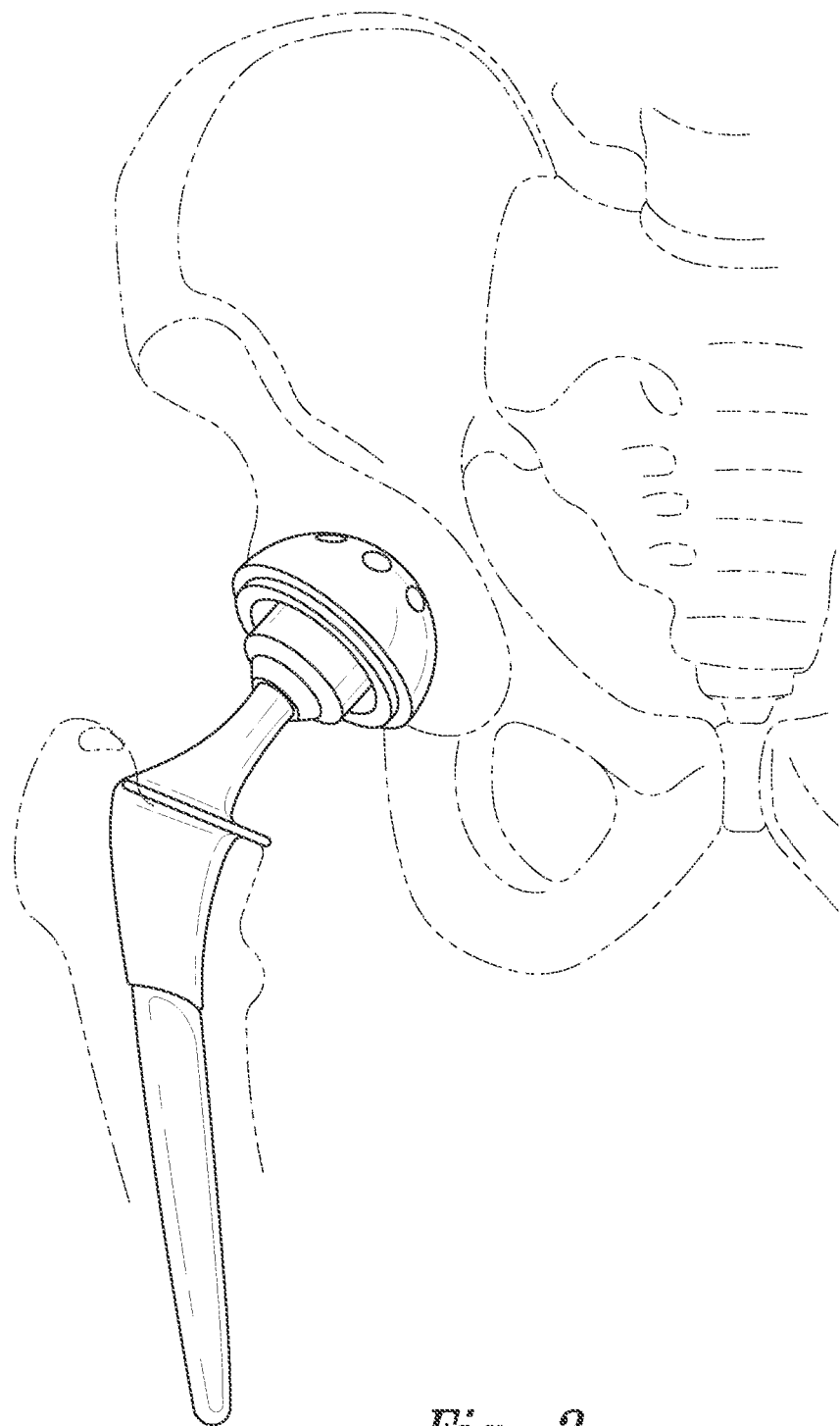
FIG. 3 shows the total hip replacement within the pelvis of a patient.

Briefly stated the present invention provides a variety of hip replacements that can be utilized to monitor the integrity and efficaciousness of the device. Prior to setting forth the invention however, it may be helpful to an understanding thereof to first set forth definitions of certain terms that are used hereinafter.

"Hip replacement" as that term is utilized herein, may take a variety of different forms and may involve replacement of all or portions of the patient's hip joint with synthetic materials. In total hip replacement (THR), both the femoral head and the acetabulum are replaced. In a hemi (partial) hip arthroplasty, only the femoral head is replaced while the patient's own acetabulum is retained. The femoral component of a hip replacement may be a single piece with the head and stem as an integral, complete unit, or it may be constructed in several pieces, such as a femoral stem which is then coupled to a separate femoral head piece and neck section (which is often done to provide the patient with custom fitting for length and/or femoral head size). The femoral component can be cemented in place with PMMA bone cement (cemented hip) or it can be fitted precisely within the medullary canal of the femur and held in place without cement (AML—anatomic medullary locking—stem design). Similarly, the acetabular component of a THR can also be a single piece coupled to the hip socket to receives the femoral head, or be a two-piece component with a shell coupled to the pelvic bone and an inner liner attached to the shell. The acetabular component of a THR can be held in place with screws and/or cement or it can be affixed without cement.

Currently, the various components may be made of the same material, for example, all portions can be made of metal, or individual components can be made from a variety of different materials. For example, it is common for the acetabular component to have a metal shell with an outer surface coating to facilitate bone attachment and ingrowth, and an inner lining made from polyethylene, ultrahigh molecular weight polyethylene, ceramic, or surgical-grade stainless steel. Similarly, there may be several different combinations of materials used in the construction of the femoral head. For example, the femoral head can be composed of metal, usually cobalt chromium (but also stainless steel or titanium), or a ceramic material, while the femoral stem is typically metal (stainless steel, titanium, or cobalt chromium) and often possesses a surface coating to encourage incorporation of the implant within the femur.

As utilized herein the terms "hip implant" or "hip replacement" or "hip replacement or portion thereof" or "medical device" should be understood, unless the specific context requires otherwise, to refer to any or all of the various components that go into making a total hip prosthesis, including for example, the femoral stem, femoral head, and acetabular assembly, as well as their various sub-components. "Hip replacement prosthesis" should be understood to refer to either a partial or total hip replacement prosthesis.

"Sensor" refers to a device that can be utilized to measure one or more different aspects of a body, of a hip implant inserted within a body, and/or the integrity, impact, efficaciousness or effect of the hip implant inserted within a body. Representative examples of sensors suitable for use within the present invention include, for example, fluid pressure sensors, contact sensors, position sensors, pulse pressure sensors, blood volume sensors, blood flow sensors, chemistry sensors (e.g., for blood and/or other fluids), metabolic sensors (e.g., for blood and/or other fluids), accelerometers, mechanical stress sensors and temperature sensors. Within certain embodiments the sensor can be a wireless sensor, or, within other embodiments, a sensor connected to a wireless microprocessor. Within further embodiments one or more (including all) of the sensors can have a Unique Sensor Identification number ("USI") which specifically identifies the sensor.

A wide variety of sensors (also referred to as Microelectromechanical Systems or "MEMS", or Nanoelectromechanical Systems or "NEMS", and BioMEMS or BioNEMS, see generally https://en.wikipedia.org/wiki/MEMS) can be utilized within the present invention. Representative patents and patent applications include U.S. Pat. No. 7,383,071 and U.S. Publication No. 2010/0285082. Representative publications include "Introduction to BioMEMS" by Albert Foch, CRC Press, 2013; "From MEMS to Bio-MEMS and Bio-NEMS: Manufacturing Techniques and Applications by Marc J. Madou, CRC Press 2011; "Bio-MEMS: Science and Engineering Perspectives, by Simona Badilescu, CRC Press 2011; "Fundamentals of BioMEMS and Medical Microdevices" by Steven S. Saliterman, SPIE—The International Society of Optical Engineering, 2006; "Bio-MEMS: Technologies and Applications", edited by Wanjun Wang and Steven A. Soper, CRC Press, 2012; and "Inertial MEMS: Principles and Practice" by Volker Kempe, Cambridge University Press, 2011; Polla, D. L., et al., "Microdevices in Medicine," Ann. Rev. Biomed. Eng. 2000, 02:551-576; Yun, K. S., et al., "A Surface-Tension Driven Micropump for Low-voltage and Low-Power Operations," *J. Microelectromechanical Sys.*, 11:5, October 2002, 454-461; Yeh, R., et al., "Single Mask, Large Force, and Large Displacement Electrostatic Linear Inchworm Motors," *J. Microelectromechanical Sys.*, 11:4, August 2002, 330-336; and Loh, N. C., et al., "Sub-10 $cm^3$ Interferometric Accelerometer with Nano-g Resolution," *J. Microelectromechanical Sys.*, 11:3, June 2002, 182-187; all of the above of which are incorporated by reference in their entirety.

In order to further understand the various aspects of the invention provided herein, the following sections are provided below: A. Medical Uses of Hip Implants; B. Representative Embodiments of Hip Implants; C. Coatings on Hip Implants; D. Drug-Eluting Hip Implants; E. Methods for Monitoring Infections in Hip Implants; F. Generation of Power; G. Medical Use of Sensors; H. Medical Imaging and Self-Diagnosis of Assemblies Comprising Hip Implants, Predictive Analysis and Predictive Maintenance; I. Methods of Monitoring Assemblies Comprising Hip Implants; and J. Collection, Transmission, Analysis, and Distribution of Data from Assemblies Comprising Hip Implants.

A. Medical Uses of Hip Replacements

Hip replacement is carried out when the patient loses sufficient use of the hip so as to result in disability, loss of movement and function, impaired ambulation, and/or continuous joint pain and discomfort. Common causes of impaired hip function leading to total or partial hip replacement include trauma (typically a hip fracture; often at the femoral neck), avascular necrosis of the hip, or various types of arthritis (such as rheumatoid arthritis or osteoarthritis). In most patients, the operation is successful in improving ambulation, restoring function and reducing pain; as a result, it is one of the most common orthopedic procedures in the Western World.

B. Representative Embodiments of Hip Implants

Figure 4:
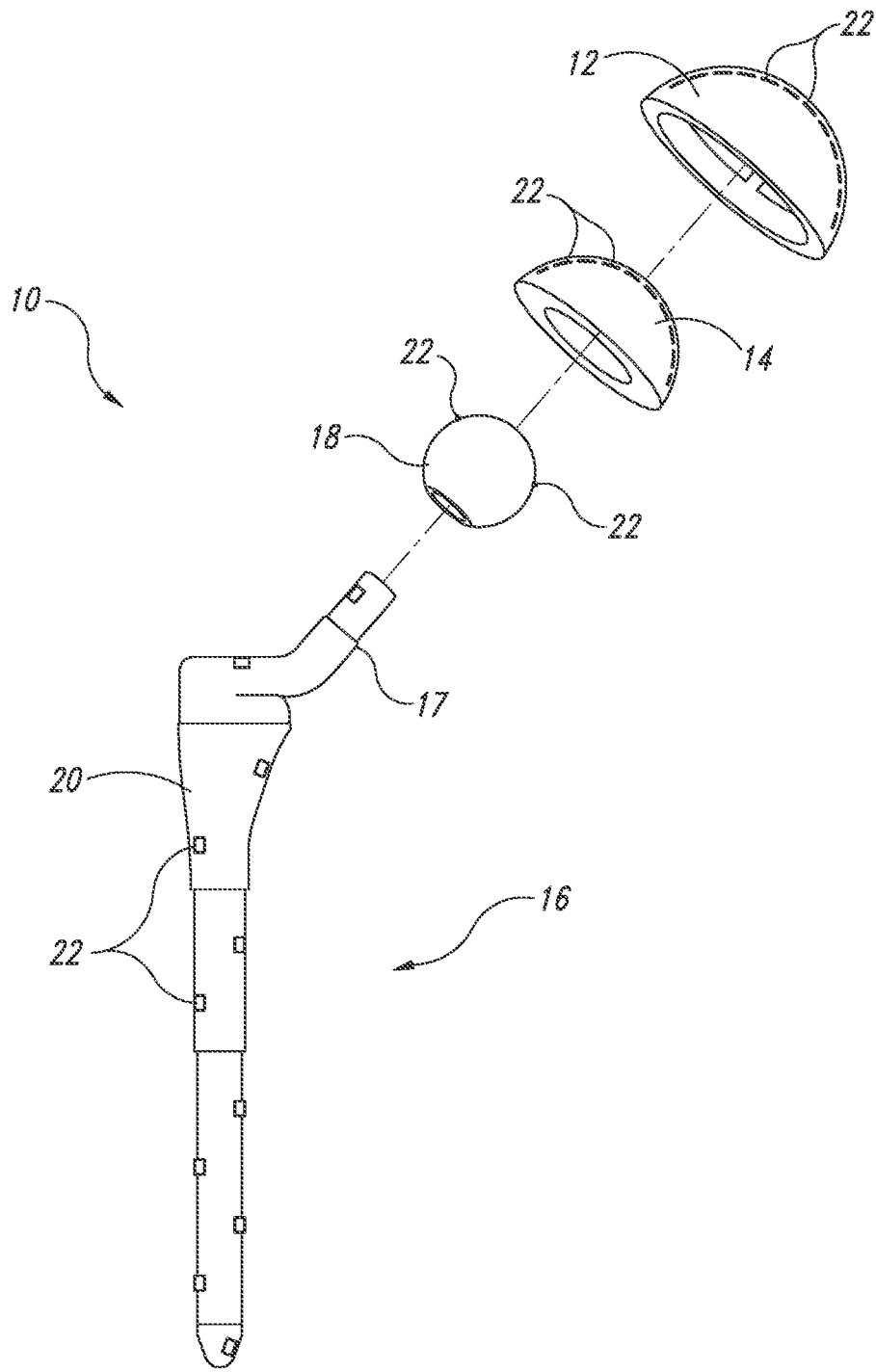
FIG. 4 is an exploded view of a total hip having sensors thereon according to various embodiments as described herein.

FIG. 4 illustrates a prosthesis 10 in the form of a replacement hip having one or more sensors 22 as described herein. The replacement hip includes an acetabular shell 12 in which an acetabular liner 14 is placed. It also includes a femoral assembly 16 which includes two components, a femoral head 18 and a femoral implant or femoral stem 20 (also having a femoral neck 17).

Figure 5:
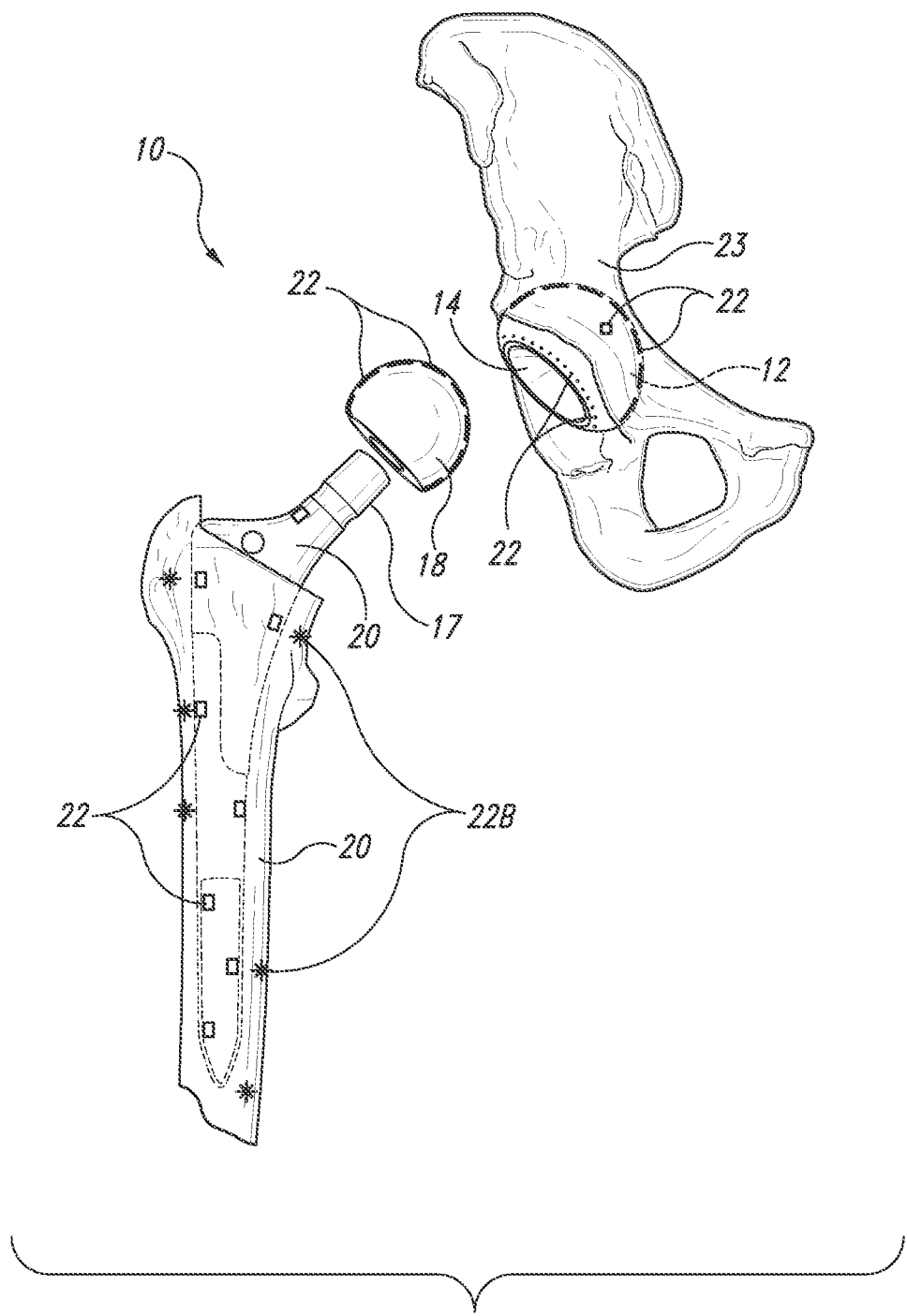
FIG. 5 illustrates the embodiment of FIG. 4 after the hip has been replaced showing contact locations with the bones of the patient.

FIG. 5 shows the hip replacement prosthesis 10 as positioned in a patient, in an exploded view. As shown in FIG. 5, the acetabular shell 12 is fixed to the pelvis bone 23. The femoral stem 20 is coupled to the femur 24 and the femoral head 18 is shown ready for positioning on the femoral stem 20 and also for entering the liner 14 of the acetabular shell. FIGS. 4 and 5 will be described jointly in order to illustrate various embodiments.

A plurality of sensors 22 are positioned in the prosthesis 10 in order to monitor, in situ, the real-time operation of the patient activity and the prosthesis performance. A variety of these sensors will now be described according to various embodiments.

In one embodiment, contact sensors 22 are provided on the outer surface of the acetabular shell 12. These sensors 22 detect and record contact between adjacent parts, such as the between the acetabular shell 12 and the pelvis 23 and/or between the acetabular shell and the bone cement (if present) and/or between the bone cement (if present) and the pelvis. The contact sensors 22 can detect loosening of the prosthesis 10 and its connection to the surrounding cement (if present) and/or pelvic bone. Loosening of the acetabulum is a common complication that occurs (typically over 8-12 years) when bone loss takes place in the pelvic bones surrounding the acetabulum (e.g., due to a process known as osteolysis). Erosion of the bone around the implant may be caused by material debris (metal, ceramic, and/or polyurethane fragments) generated by friction between the femoral head and acetabular cup entering the pelvic tissues surrounding the acetabulum and causing inflammation and bone loss. Other potential causes of inflammation and osteolysis are implant vibration and motion, mechanical wear and tear, lack of biocompatibility between the implant materials and the surrounding bone, metal allergy, and lack of biocompatibility between the bone cement and the surrounding bone. In addition, the contact sensors 22 may indicate that the acetabular shell 12 is positioned further from the pelvic bone 23 than desired as a result of material debris being built up over time and/or the presence of inflammation between the shell and the pelvic bone. A plurality of contact sensors 22 are positioned at different locations around the acetabular shell 12. In the example shown, a number of sensors are shown positioned on the outer surface of the acetabular shell 12. In various embodiments, these sensors may be positioned in a variety of different patterns based on the contact locations to the pelvis bone and/or the surrounding bone cement (if present). For example, they may be arranged in the pattern of an X, as oval or concentric rings around the acetabular shell from the outermost circumference to the crown or in various other patterns, in order to collect accurate data on the physical contact between the acetabular shell 12 and the pelvic bone 23 and/or surrounding bone cement (if present). Contact sensors can also be dispersed within/arranged within the bone cement (if present) so as to collect data on the physical contact between the bone cement and the acetabular prosthesis and/or between the bone cement and the pelvic bone. Within various embodiments, Contact sensors 22 may also be positioned at various locations on the two surfaces of the acetabular liner 14. The contact sensors 22 can therefore sense the contact (and/or movement) between the acetabular liner and the acetabular shell (these sensors could be "paired" so as to detect shifting between the acetabular liner and shell), as well as contact between the femoral head and the acetabular liner. Similarly contact sensors 22 can be positioned at various locations on the femoral head to detect contact between the femoral head and the acetabular liner. Thus, in the embodiment of FIGS. 4 and 5, a variety of contact sensors are provided in order to monitor contact between the bone and the acetabular component, and between the femoral head and the acetabular liner. Dislocation of the femoral head from the natural or synthetic acetabulum of a prosthetic hip is a common complication of hip replacement occurring shortly after surgery (particularly while the surrounding supportive tissues are healing from surgery); sensors on the femoral head and/or acetabulum can alert the patient and the healthcare provider if joint dislocation has occurred. Partial or incomplete dislocation (subluxation) of the hip joint can also occur and may not be readily evident to the patient or the physician; contact sensors on the femoral head and/or acetabulum can determine of the joint is functioning (tracking) correctly and if subluxation (even if subclinical or asymptomatic) is occurring.

Additional contact sensors can be positioned on the femoral stem as well, to monitor contact between the femoral stem and the femur and/or contact between the femoral stem and the surrounding bone cement (if present). Contact sensors can also be dispersed within/arranged within the bone cement (e.g., 22B. if present) so as to collect data on the physical contact between the bone cement and the femoral prosthesis and/or between the bone cement and the femoral canal. These sensors 22 and 22B can detect and record contact between connecting parts in a modular femoral prosthesis, such as the between the femoral head 18, femoral neck 17 and/or the femoral stem 20. These sensors, which can be arranged in corresponding pairs on adjacent pieces, can be used to insure that the connecting elements of a modular femoral prosthesis are properly aligned and fitted. Sensors on the femoral shaft 20 can be used to monitor the contact between the femoral shaft and the femur and/or the contact between femoral shaft and the surrounding bone cement (if present); sensors in the bone cement can be used to monitor the contact between the bone cement (e.g., 22B, if present) and the femur. The contact sensors on the femoral shaft 22 can detect loosening of the prosthesis and its connection to the surrounding cement (if present) and/or the femur. Loosening of the femoral shaft is a common complication that occurs when (typically over 8-12 years), bone loss occurs in the femoral canal surrounding the femoral shaft due to osteolysis. As described above, erosion of the bone around the implant may be caused by material debris (metal, ceramic, and/or polyurethane fragments) generated by friction between the femoral head and acetabular cup entering the femoral tissues surrounding the femoral prosthesis and causing inflammation and bone loss. Other potential causes of inflammation and osteolysis are implant vibration and motion, mechanical wear and tear, lack of biocompatibility between the implant materials and the surrounding bone, metal allergy, and lack of biocompatibility between the bone cement and the surrounding bone. A plurality of contact sensors 22 are positioned at different locations around the femoral shaft. As shown in FIGS. 4 and 5, sensors are shown positioned on the outer surface of the femoral shaft. In various embodiments, these sensors may be positioned in a variety of different patterns based on the contact locations to the femoral canal and/or the surrounding bone cement (if present). For example, they may be arranged in the pattern of a helix, as vertical lines or concentric rings around the femoral shaft or in various other patterns, in order to collect accurate data on the physical contact between the femoral shaft 20 and the femur and/or surrounding bone cement (if present). Within various embodiments of the invention contact sensors are placed on the femoral shaft, and the femur and/or bone cement at a density of greater than one, two, three, four, five, six, seven, eight, nine, or ten sensors per square centimeter, or, per cubic centimeter of the device.

Figure 6A:
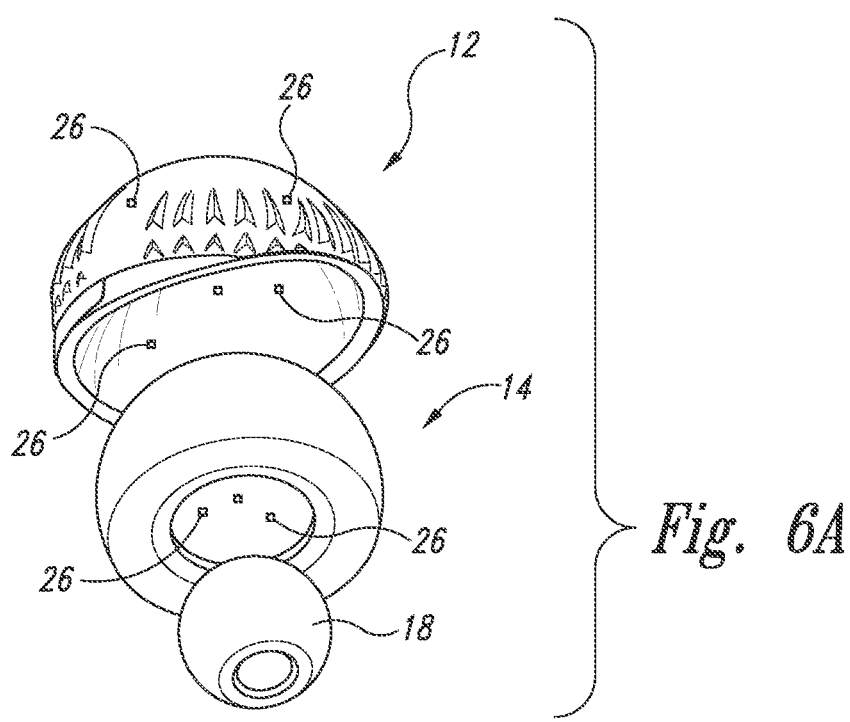
FIG. 6A is an exploded view of the acetabular cup, a liner, and the femoral having various sensors thereon according to the various embodiments described herein.

FIG. 6A illustrates an exploded version of the acetabular shell 12, the liner 14, and the femoral head 18 to permit clear illustration of various positions for strain gauges 26 that can be positioned on the prosthesis. The contact sensors 22 are not shown in FIG. 6, but could be used concurrently with the strain gauges and be positioned adjacent to each other or be the same sensor. Strain gauges 26 may be positioned at various locations on the acetabular shell 12 to detect strain encountered between the prosthesis and the surrounding bone. A decrease in strain may indicate that there is bone resorbtion (loss), which could lead to loosening of the prosthesis, or fractures. The strain sensors 26 provide a different data point than the contact sensors 22. The contact sensors 22 merely specify whether there is current contact between adjacent structures and thus provide a good indication of whether there is abutting contact between two surfaces. However, they do not provide an indication of the strain that is present in either of the surfaces, on the other hand, the strain sensors 26 output data indicative of the mechanical strain forces being applied across the implant which, if not corrected, can be a harbinger of future loosening and prosthesis failure. In addition, the strain gauges 26 may be of the type which indicates the strain which is being exhibited between two surfaces, such as between the acetabular liner and the pelvic bone or between the acetabular shell 12 and the acetabular liner 14. Further, such strain gauges may collect data regarding the strain and location of such strain between the femoral head 18 and the acetabular liner 14.

Figure 6B:
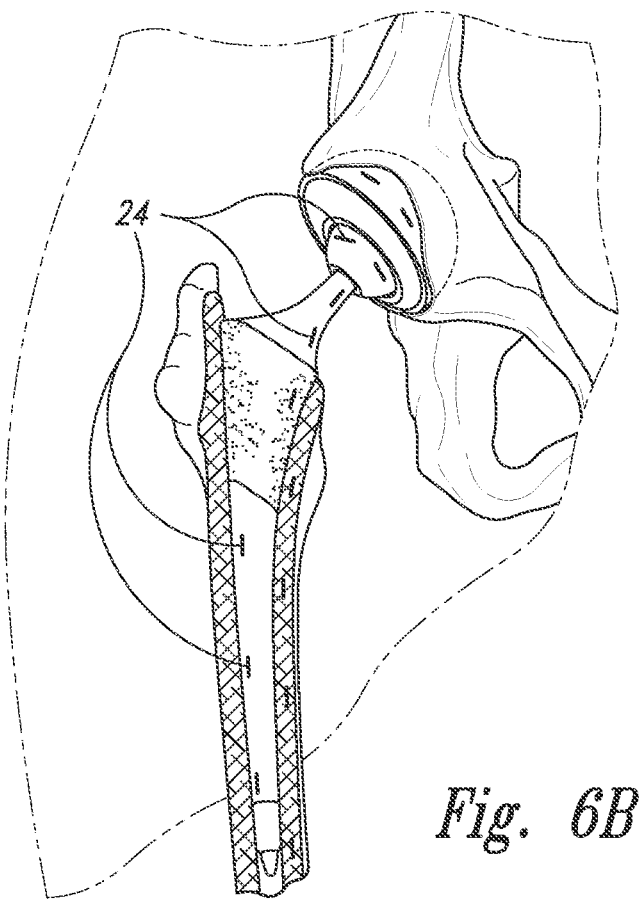
FIG. 6B is an illustration of the incorporation of strain gauges in a variety of locations.

As shown in FIG. 6B, strain gauges can be located on the femoral prosthesis; particularly the femoral stem, but also the femoral neck and the femoral head. Strain gauges may be positioned at various locations on the femoral stem to detect strain encountered between the prosthesis and the surrounding bone. A decrease in strain may indicate that there is bone resorbtion (loss) in the femoral canal, which could lead to loosening of the prosthesis, or femoral fractures. The strain sensors can provide an indication of the strain that is present in the femoral shaft and measure the most important mechanical strain forces being applied across the implant which, if not corrected, have a high probability of resulting in loosening and prosthesis failure. Within various embodiments of the invention strain sensors are placed on the acetabular shell, acetabular liner, femoral shaft, and the femur and/or bone cement at a density of greater than one, two, three, four, five, six, seven, eight, nine, or ten sensors per square centimeter, or, per cubic centimeter of the device.

FIGS. 7A and 7B illustrate one embodiment in which accelerometers are positioned at various locations in and on the femoral shaft 18, femoral neck and femoral head. In particular, as shown in FIG. 7A one or more accelerometers may be positioned on the femoral head 16. In addition, one or more acceleration sensors 42 in the form of accelerometers or gyroscopes can be positioned on the surface of or inside the femoral shaft portion 18. Accelerometers provide the benefit of being able to detect acceleration, vibration, shock, tilt, and rotation of various components. They permit the ability to measure performance of the prosthesis 10 under various conditions and over long periods of time. In this particular example, the prosthesis 10 is a hip replacement joint. Of course, it could be any other prosthesis, such as a prosthetic elbow joint, shoulder joint, metacarpal joint, ankle joint, or the like. Within various embodiments of the invention strain sensors are placed on the acetabular shell, acetabular liner, femoral shaft, and the femur and/or bone cement at a density of greater than one, two, three, four, five, six, seven, eight, nine, or ten sensors per square centimeter, or, per cubic centimeter of the device.

Shortly after the hip has been replaced, the leg will be mobilized, at first passively, then actively; shortly thereafter, the patient will begin gradual weight bearing on the joint. The accelerometers 42 will measure the movement of the hip socket during movement, including during ambulation as the leg swings forward, hits the ground, plants, is lifted off the ground, and the body is propelled forward. In addition, the accelerometers will measure the impact of the foot hitting the ground and the effect of the force being transferred through the femur to the pelvic bones and any vibration, shock or rotation which may occur at different locations in the prosthesis 10. As the patient continues to improve their range of motion postoperatively, the acceleration experienced at different locations in the prosthetic hip joint, can be monitored. It will be expected that as the patient heals from the surgery, activity levels will progressively increase, ambulation will improve, steps will be more rapid (and fluid) and, in addition, greater stride length will be achieved with each step. This may result in greater impact every time the foot hits the ground, which can be measured over time (and compared to previous values) by the various accelerometers 42 positioned on the femoral head 16, in the femoral stem 18 and in other locations on the prosthesis 10. Postoperative progress can be monitored (readings compared from day-to-day, week-to-week, etc.) and the information compiled and relayed to both the patient and the attending physician allowing rehabilitation to be followed sequentially and compared to expected (typical population) norms. Within certain embodiments, a wearable device interrogates the sensors on a selected or randomized basis, and captures and/or stores the collected sensor data. This data may then be downloaded to another system or device (as described in further detail below).

Integrating the data collected by the sensors described herein (e.g., contact sensors, strain gauges and/or accelerometers) with simple, widely available, commercial analytical technologies such as pedometers and global positioning satellite (GPS) capability, allows further clinically important data to be collected such as, but not restricted to: extent of patient ambulation (time, distance, steps, speed, cadence), patient activity levels (frequency of activity, duration, intensity), exercise tolerance (work, calories, power, training effect), range of motion (discussed later) and prosthesis performance under various "real world" conditions. It is difficult to overstate the value of this information in enabling better management of the patient's recovery. An attending physician (or physiotherapist, rehabilitation specialist) only observes the patient episodically during scheduled visits; the degree of patient function at the exact moment of examination can be impacted by a multitude of disparate factors such as: the presence or absence of pain, the presence or absence of inflammation, stiffness, time of day, compliance and timing of medication use (pain medications, anti-inflammatories), recent activity and exercise levels, patient strength, mental status, language barriers, the nature of their doctor-patient relationship, or even the patient's ability to accurately articulate their symptoms—to name just a few. Continuous monitoring and data collection can allow the patient and the physician to monitor progress objectively by supplying information about patient function under numerous conditions and circumstances, to evaluate how performance has been affected by various interventions (pain control, exercise, physiotherapy, anti-inflammatory medication, rest, etc.), and to compare rehabilitation progress versus previous function and future expected function. Better therapeutic decisions and better patient compliance can be expected when both the doctor and the patient have the benefit of observing the impact of various treatment modalities on patient rehabilitation, activity, function and overall performance.

The sensor used for the contact, strain and accelerometers can be an acceptable type of those generally available (see e.g., U.S. Pat. Nos. 7,450,332; 7,463,997 and 7,924,267 which describe various types of such sensors, including MEMs sensors that can act as strain gauges, accelerometers and many other sensing functions). The particular sensor described in U.S. Pat. No. 7,450,332, which detects free fall of an object and motion of an object with respect to a gravity field, would have particular benefits in being able to detect and store all the forces acting on the leg and the full motion of the leg, during passive and active motion and when it is swinging in between steps, both before, after and during impact with the ground.

FIGS. 7A, 8A and 8B illustrate yet another type of sensor, articular surface wear sensors 46 that may be positioned at various locations in the acetabular liner and the femoral head. According to one embodiment, one or more articular surface wear sensors are positioned at various depths of the acetabular liner 14 as shown in FIGS. 7A and 8B and/or the femoral head 16. These sensors 46 for measuring the surface wear may be contact pressure sensors that are embedded within the acetabular liner and/or femoral head at varying depths in order to monitor articular surface erosion (and provide data as to the extent and depth of surface wear of the two components). They may also be positioned between the acetabular shell 12 and the acetabular liner 14 as shown in FIGS. 8A and 8B in order to monitor any kind of wear or degradation of the physical contact between the shell 12 and the liner 14.

Figure 9:
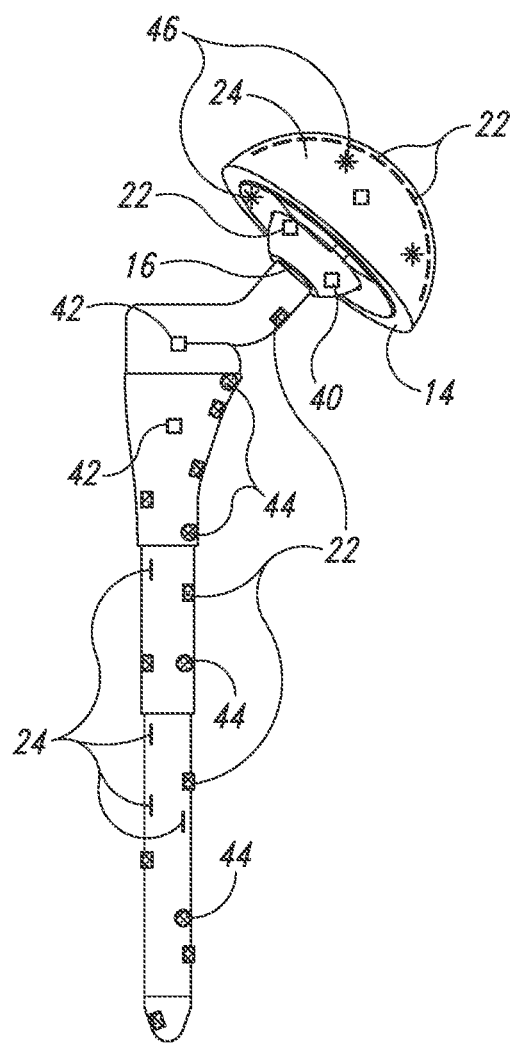
FIG. 9 is a side view of a total assembled hip with examples of different sensor locations.

FIG. 9 shows an example of the complete prosthesis in the form of a hip replacement prosthesis having a plurality of different sensors (e.g., 22, 24, 42, 44, and 46) thereon. It may include, in a single prosthesis hip 10, a plurality of contact sensors 22, strain gauges 24, accelerometers 42, articular wear surface sensors 46, as well as electric power generation structure 44. In addition, a plurality of position sensors can also be placed to monitor, record and transfer the exact position of the head 18 relative to the acetabular liner 14.

Figure 10:
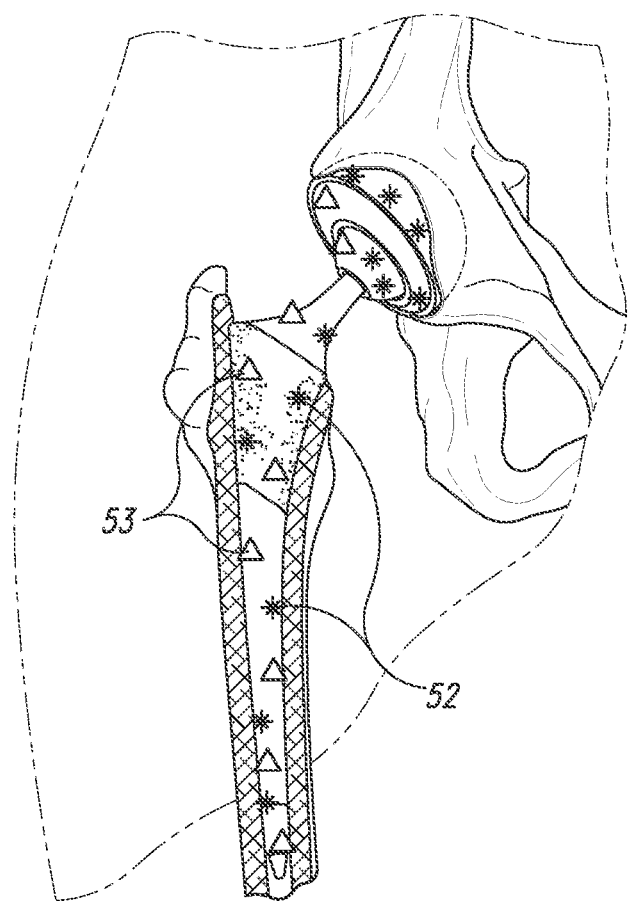
FIG. 10 shows the completed hip assembly of FIG. 9 fully functional in a patient, with the various different types of sensors.

FIG. 10 illustrates different locations at which position sensors 52 and/or accelerometers 53 may be located in the prosthesis. The position sensors 52, as well as accelerometers 53, can be contained within the femoral stem or within the neck, or within the femoral head, both proximally and distally. They can also be contained within the acetabular component, both the liner and the shell. By placing position sensors and/or accelerometers along the length of the femoral stem, the exact location of the femur as compared to the acetabular component and to the pelvis can be exactly determined and stored in memory. Similarly, by placing accelerometers at different locations in the neck and the head of the femoral implant, the amount of pressure applied at different locations, the movement at the locations and the relative positions of the components to each other can be exactly determined. Similarly, such sensors enhance the accuracy of a physical exam and provide for the ability to detect full dislocation or partial dislocation (subluxation) of the hip joint.

C. Coatings on Hip Implants

Within certain embodiments of the invention the hip implants are provided that can have one or more coatings on one or more surfaces of the hip implant. Coatings can be provided on hip implant for a variety of purposes. Coatings may be biodegradable, or non-biodegradable, or a combination of these. Representative examples of coatings are polymer-based (e.g., polymers comprised of polyurethane, polyester, polylactic acid, polyamino acid, polytetrafluoroethylene, tephlon, Gortex®), although non-polymer coatings may also be utilized. Within certain embodiments of the invention, one or more sensors as described herein may be disbursed throughout the coating (e.g., even in a random manner).

D. Drug-Eluting Hip Implants

Within certain embodiments of the invention drug-eluting hip implants are provided which comprise one or more sensors, and which can be utilized to release a desired agent (e.g., a drug or therapeutic agent) to a desired location within the body. Representative examples of suitable anti-scarring or anti-fibrotic drugs include disclosed in U.S. Pat. No. 5,716,981; US Patent App. Nos. 2005/0021126 and 2005/0171594; and US Patent App. Nos. 2005/0181005 and 2005/0181009, all of which are incorporated by reference in their entirety.

Within related embodiments, a drug-eluting delivery device may be included within the hip implant in order to release a desired drug upon demand (e.g., upon remote activation/demand, or based upon a timed schedule, see generally U.S. Patent App. No. 2011/0092948 entitled "Remotely Activated Piezoelectric Pump For Delivery of Biological Agents to the Intervertebral Disc and Spine", which is incorporated by reference in its entirety), or upon detection of an activating event (e.g., detection of a leak by a pressure sensor). For example, within certain embodiments of the invention biological agents can be administered along with or released from a hip implant in order to treat or prevent disease (e.g., i) in the case of cancer with a chemotherapeutic agent, or in the case of preventing restenosis, or ii) in the case of infection, with an anti-microbial drug).

Within preferred embodiments one or more sensors (e.g., pressure sensors, contact sensors, and/or position sensors) can be utilized to determine appropriate placement of the desired drug, as well as the quantity and release kinetics of drug to be released at a desired site.

E. Methods for Monitoring Infection

Within other embodiments hip implants are provided comprising one or more temperature sensors. Such hip implants can be utilized to measure the temperature of the joint, the hip implant, and in the local tissue and environment adjacent to the hip implant. Methods are also provided for monitoring changes in temperature over time, in order to determine and/or provide notice (e.g., to a patient and/or a healthcare provider) that an infection may be imminent.

In certain embodiments of the present invention, metabolic and physical sensors can be utilized to monitor for rare, but potentially life-threatening complications of joint replacement surgery. In a small number of patients (<1%), the prosthetic joint and surrounding tissues can become infected; typically from bacteria colonizing the patient's own skin that contaminate the surgical field (often *Staphylococcus aureus* or *Staphylococcus epidermidis*). Sensors such as temperature sensors (detecting temperature increases), pH sensors (detecting pH decreases), and other metabolic sensors can be used to suggest the presence of infection on or around the implant. Early detection of infection could allow preemptive treatment with antibiotics or surgical drainage and eliminate the need to surgically remove the prosthesis.

F. Generation of Power

FIG. 7B illustrates a particular benefit that can be obtained as the patient ambulates with the new prosthetic hip. As shown in FIG. 7B, a small electrical generation unit 44 can be positioned along an outer, or alternatively an inner, surface of the femoral stem 18. In particular, every time a user takes a step, there is a release of pressure and an increase of pressure inside the internal structure of the femoral stem 16. Using the appropriate piezoelectric materials or microelectric generators, a small amount of electricity can be generated with each step that is taken. The electricity can be stored in capacitors also mounted inside the femoral stem 16. The electricity can then be used to power the sensors that are positioned at the various locations inside the prosthesis.

A variety of techniques have been described for scavenging power from small mechanical movements or mechanical vibration. See, for example, the article entitled "Piezoelectric Power Scavenging of Mechanical Vibration Energy," by U. K. Singh et al., as published in the Australian Mining Technology Conference, Oct. 2-4, 2007, pp. 111-118. This paper provides examples of different types of power scavengers which can produce electricity from very small motion and store the electricity for later use. The above article also describes embodiments in which pressure is applied and released from the particular structure in order to produce electricity without the need for motion, but rather as a result of the application of high pressure. As explained in the embodiments herein, force is applied to the internal structure of the femoral stem 16 when the patient puts his weight on the leg during a step and such force can produce more than enough electric power to operate all of the sensors which are described herein. Other mechanisms that can produce electricity from very small amounts of repetitive motion are described U.S. Patent Application Publication No. 2010/0164705, published on Jul. 1, 2010. This patent application describes techniques by which energy can be harvested in the rotation of a tire and then the harvested energy can be used to power a plurality of different sensors and then, at selected time periods, the selected sensors can output the collected data to a central collection site. Other sensors of this type are described in issued U.S. Pat. No. 7,603,894, entitled "Self-Powered Tire Monitoring System."

In one preferred embodiment, the electrical generation system is motionless and relies solely on pressure that is applied during the step and the release of that pressure when the step is completed and the leg swings free for the next step. Since there is no motion, the patent will not feel any sensation due to small changes in the position or length of the femoral stem 18 during the step. Rather, the length is kept constant and the electricity is generated by piezoelectric structures or by internal suspended structures which do not form part of the support structure of the femoral stem 18.

Other techniques may also be utilized to scavenge for power, include, for example, those disclosed in an article entitled "Next Generation Micro-power Systems by Chandrakasan et al., as published in the 2008 Symposium on VLSI Circuits Digest of Technical Papers, pp. 1-5, (see also U.S. Pat. No. 8,283,793 entitled "Device for Energy Harvesting within a Vessel," and U.S. Pat. No. 8,311,632 entitled "Devices, Methods and Systems for Harvesting Energy in the Body,") all of the above of which are incorporated by reference in their entirety.

After the electricity is generated by one or more generators 44, the electricity is transmitted to any one of the variety of sensors which is described herein. For example, it can be transmitted to the contact sensors 22, the strain gauges 24, or the accelerometers 42. It may also be transmitted to the other sensors that will be described later herein. The transmission of the power can be carried out by any acceptable technique. For example, if the sensor is physically coupled to the femoral stem electric wires may run from the generator 44 to the particular sensor, for example accelerometers 42 or other surface wear structures that are part of the femoral stem. For those sensors which are in the acetabular component, the electricity can be transmitted wirelessly in the same way that wireless smartcards receive power from closely adjacent power sources using the appropriate send and receive antennas. Such send and receive techniques of electric power are also described in the publication and the patent applications and issued U.S. patent previously described, all of which are incorporated herein by reference.

G. Medical Use of Sensors

Figure 11A:
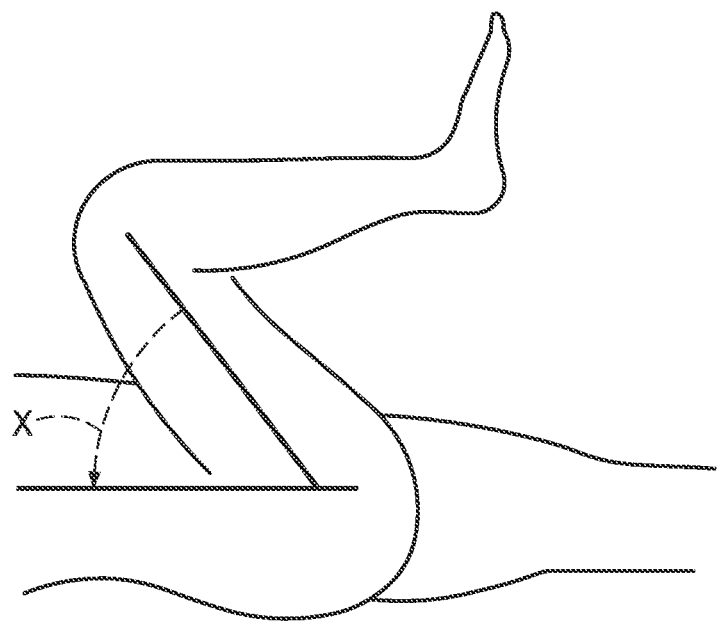
FIGS. 11A and 11B illustrate different types of hip movement which may be measured and monitored according to various embodiments as disclosed herein.
Figure 11B:
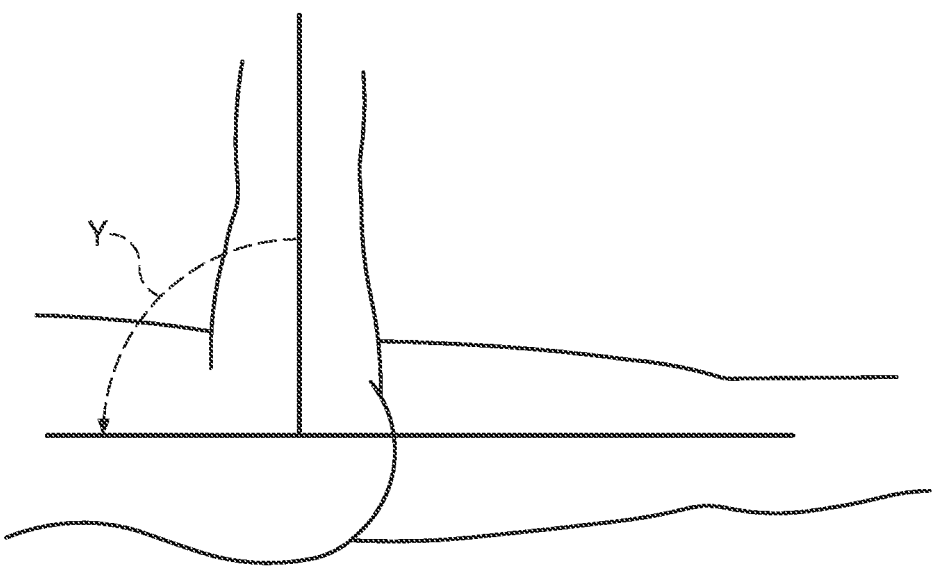

FIGS. 11A and 11B indicate examples of uses of the sensors during a physical examination of the patient and the different types of data which may be obtained from the sensors which have been implanted according to the teachings herein. The sensors provide evaluation data on the range of motion (ROM) of the hip. Currently, ROM is usually measured clinically by the physician passively moving the hip joint through a full range of motion during physical examination and recording the results (degrees of flexion, extension, abduction, adduction, external rotation, internal rotation and rotation in flexion). Motion sensors and accelerometers can be used to accurately determine the full ROM of the prosthetic hip joint both during physical examination and during normal daily activities between visits. As shown in FIG. 11A, one primary factor in the health of the hip is the angle X that the patient is able to achieve at various times during physical therapy as they recover from the surgery. As the angle X becomes smaller and smaller, the doctor can be assured that joint function is improving. By tracking angle X over time the physical therapist can monitor the progress of the patient, assess whether scar tissue formation, subluxation, or other pathology is limiting/affecting ROM of the hip, and change/implement treatment as needed. With the sensors installed as indicated herein, the physical therapist or physician does not need to guess the angle being achieved, rather, if the leg is positioned adjacent to a read out computer, the exact angle can be known at the very moment that the joint is being clinically evaluated. On the other hand, if X does not continue to decrease, but remains large (or increases), the physical therapist or physician can be alerted to problems which the patient may be having in rehabilitation or delayed recovery from the surgery and can investigate and/or take action sooner rather than later. Similarly, the embodiment of FIG. 11B indicates measurements that can be taken when the user holds the leg at exactly a 90° angle Y as shown. With the leg held firmly at 90°, data can be collected from the various sensors throughout the leg in order to determine the strain, the contact locations, acceleration and other data. The position sensors as used herein can alert the patient that the leg is held at exactly 90° so that the collecting of the data can be accurate as data is collected at different times over several months as the patient is monitored. While flexion and extension are illustrated in the sited figures, it should be obvious to one of skill in the art that data can also be collected for abduction, adduction, external rotation, and internal rotation and rotation in flexion of the hip. Additionally, ROM can also be monitored between patient visits by interpreting ROM generated during daily activities when the patient is at home.

Some aspects of the operation and the benefits obtained thereby will now be explained. One particular benefit is the live and in-situ monitoring of the patient's recovery and the hip implant 10. The sensors as described herein are collecting data on a constant basis, during normal daily activities and even during the night if desired. Namely, the strain will be measured, collected and stored on a regular basis over long periods of time with particular measurements being taken at regular intervals. For example, the contact sensors can obtain and report data once every 10 seconds, once a minute, or once a day. Other sensors will collect data more frequently, such as several times a second. For example, it would be expected that the acceleration and position data would be collected and stored several times a second. Other types of data might only need to be collected by the minute or by the hour. Since the femoral stem contains a large internal portion which, in the prior art might be hollow or a solid bar of metal, this internal structure has more than sufficient space in order to house one or more processor circuits, CPUs, memory chips and other electrical circuits as well as antennas for sending and receiving the data. The processors can be programmed to collect data from the various sensors on any desired schedule as set by the medical professional. All activity can be continuously monitored post operation and the data collected and stored in the memory located inside the femoral stem 18.

A patient will generally have regular medical checkups. When the patient goes to the doctor's office for a medical checkup, the doctor will bring a reading device closely adjacent the implant 10, in this example a hip replacement, in order to transfer the data from the internal circuit inside the femoral stem 18 to the database in the physician's office. The use of wireless transmission using smartcards or other techniques is very well known in the art and need not be described in detail. Examples of such wireless transmission of data are provided in the published patent applications and patents which have been described herein. The data which has been collected based on the patient's movement and use of the leg over the prior several weeks or even several months is transferred in a few moments from the memory which is positioned in the femoral stem 18 to the doctor's computer or wireless device. The computer therefore analyzes the data for anomalies, unexpected changes over time, positive or negative trends, and other signs which indicative of the health of the patient and the operability of the prosthesis. In addition, the physician can collect data that details the record of all impacts to the joint, including the magnitude and the direction of the acceleration. If the physician locates a high acceleration event, such as the patient falling, or other physical activities or exercise, the physician can be alerted to inquire of the patient of any problems they may have had during a fall or, alternatively, warn the patient against too vigorous an activity which may potentially cause damage to the hip implant. For example, if the patient has decided to go skiing or jogging, the doctor will be able to monitor the effect of such activity on the implant 10, including the accelerations and strains during the event itself. The doctor can then look at the health of the prosthesis in the hours and days after the event and compare it to data prior to the event to determine if any particular event caused long term damage, such a separation of the prosthesis from the surrounding bone tissue or joint subluxation, or if the activities subjected the implant to stress/strain/impact forces beyond the manufacturer's performance specifications for that particular artificial joint. Data can be collected and compared with respect to the ongoing and long term performance of the implant from the strain gauges, the contact sensors, the surface wear sensors, or other sensors which may be present.

In one alternative, the patient may also have such a reading device in their home which collates the data from the implant on a periodic basis, such as once per day or once per week. Empowering the patient to follow their own rehabilitation—and enabling them to see the positive (and negative) effects of various lifestyle choices on their health and rehabilitation—can be expected to improve compliance and improve patient outcomes. Furthermore, their experience can be shared via the web with other patients to compare their progress versus expected "norms" for function and rehabilitation and alert them to signs and symptoms that should be brought to their doctor's attention. The performance of different implants can be compared in different patients (different sexes, weights, activity levels, etc.) to help manufacturers design better prostheses and assist orthopedic surgeons in the selection of the right prosthesis for specific patient types. Payers, patients, manufacturers and physicians could all benefit from the collection of this comparative information. Lastly, data accumulated at home can be collected and transmitted via the Internet to the physician's office for analysis—potentially eliminating unnecessary visits in some cases and encouraging immediate medical follow-up in others.

H. Medical Imaging and Self-Diagnosis of Assemblies Comprising Hip Implants; Predictive Analysis and Predictive Maintenance The present invention provides hip implants which are capable of imaging through the use of sensors over a wide variety of conditions. For example, within various aspects of the invention methods are provided for imaging a hip implant, or an assembly comprising a hip replacement with sensors, comprising the steps of detecting the changes in sensors in, on, and or within a hip implant over time, and wherein the hip implant comprises sensors at a density of greater than 1, 2, 3, 4, 5, 6, 7, 8, 9, 10 or 10 sensors per square centimeter. Within other aspects the hip implant comprises sensors at a density of greater than 1, 2, 3, 4, 5, 6, 7, 8, 9, 10 or 10 sensors per cubic centimeter. Within either of these embodiments there can be less than 50, 75, 100, or 100 sensors per square centimeter, or per cubic centimeter. As noted above, a wide variety of sensors can be utilized therein, including for example, contact sensors, strain gauge sensors, pressure sensors, fluid pressure sensors, position sensors, pulse pressure sensors, blood volume sensors, blood flow sensors, blood chemistry sensors, blood metabolic sensors, mechanical stress sensors, and temperature sensors.

For example, a hip implant comprising sensors as described herein can be utilized to image hip anatomy through sensors which can detect positional movement. The sensors used can also include accelerometers and motion sensors to detect movement of the hip implant due to a variety of physical changes. Changes in the position of the accelerometers and/or motion sensors over time can be used as a measurement of changes in the position of the hip implant over time. Such positional changes can be used as a surrogate marker of hip anatomy—i.e. they can form an "image' of the hip implant to provide information on the size, shape and location of changes to the hip implant, and/or hip implant movement/migration. For example, loosening of the hip implant (typically in the femoral stem or acetabular shell) can result in unwanted movement of the prosthesis relative to bone in which it is implanted during activity and weight bearing. By utilizing sensors in the present invention, it is possible to determine the location of the unwanted movement and the degree of movement present during different motions and activities. Similarly, monitoring changes in the joint space (i.e. the change in the space separating the femoral and the acetabular components) over time can be used as an indicator of joint surface (femoral head and/or acetabular liner) erosion and wear. Finally, following the movement of the sensors throughout their range of motion can provide a dynamic "image" of the joint; allowing the clinician to monitor both improvement and decline in joint function (and surrounding tissues) over time.

Certain exemplary embodiments will now be explained in more detail. One particular benefit is the live and in-situ monitoring of the patient's recovery with a hip implant. The sensors as described herein can collect data on a constant basis, during normal daily activities and even during the night if desired. For example, the contact sensors can obtain and report data once every 10 seconds, once a minute, or once a day. Other sensors will collect data more frequently, such as several times a second. For example, it would be expected that the temperature, contact, and/or position data could be collected and stored several times a second. Other types of data might only need to be collected by the minute or by the hour. Still other sensors may collect data only when signaled by the patient to do so (via an external signaling/triggering device) as part of "event recording"—i.e. when the patient experiences a particular event (e.g. pain, injury, etc.)—and signals the device to obtain a reading at that time in order to allow the comparison of subjective/symptomatic data to objective/sensor data in an effort to better understand the underlying cause or triggers of the patient's symptoms.

In certain instances the hip implant is of sufficient size and has more than sufficient space in order to house one or more processor circuits, CPUs, memory chips and other electrical circuits as well as antennas for sending and receiving the data. Within other embodiments, the associated medical device may be able to house the one or more processor circuits, CPUs, memory chips and other electrical circuits as well as antennas for sending and receiving the data. Processors can be programmed to collect data from the various sensors on any desired schedule as set by the medical professional. All activity can be continuously monitored post operation or post-procedure and the data collected and stored in the memory located inside the hip implant.

A patient with a hip implant will generally have regular medical checkups. When the patient goes to the doctor's office for a medical checkup, the doctor will bring a reading device closely adjacent to the hip implant, in this example the hip implant, in order to transfer the data from the internal circuit inside the hip implant to the database in the physician's office. The use of wireless transmission using smartcards or other techniques is very well known in the art and need not be described in detail. Examples of such wireless transmission of data are provided in the published patent applications and patents which have been described herein. The data which has been collected (e.g., over a short period of time, over several weeks or even several months) is transferred in a few moments from the memory which is positioned in the hip implant to the doctor's computer or wireless device. The computer therefore analyzes the data for anomalies, unexpected changes over time, positive or negative trends, and other signs which may be indicative of the health of the patient and the operability of the hip implant. For example, if the patient has decided to go skiing or jogging, the doctor will be able to monitor the effect of such activity on the hip implant, including changes during such activities. The doctor can then look at the health of the hip implant in the hours and days after the event and compare it to data prior to the event to determine if any particular event caused long term damage, or if the activities subjected the hip implant to forces beyond the manufacturer's performance specifications for that particular hip implant. Data can be collected and compared with respect to the ongoing and long term performance of the hip implant from the strain gauges, the contact sensors, the surface wear sensors, or other sensors which may be present. One representative example of an electronic data capture, documentation and clinical decision support system (EDDS) is provided in WO 2012/061825, which is incorporated by reference in its entirety.

In one alternative, the patient may also have such a reading device in their home which collates the data from the hip implant on a periodic basis, such as once per day or once per week. As described above, the patient may also be able to "trigger" a device reading (via an external signaling/triggering device) as part of "event recording." Empowering the patient to follow their own rehabilitation—and enabling them to see the positive (and negative) effects of various lifestyle choices on their health and rehabilitation—can be expected to improve compliance and improve patient outcomes. Furthermore, their experience can be shared via the web with other patients to compare their progress versus expected "norms" for function and rehabilitation and alert them to signs and symptoms that should be brought to their doctor's attention. The performance of different hip implants can be compared in different patients (different sexes, weights, activity levels, etc.) to help manufacturers design better devices and assist surgeons and other healthcare providers in the selection of the right hip implant for specific patient types. Payers, patients, manufacturers and physicians could all benefit from the collection of this comparative information. Lastly, data accumulated at home can be collected and transmitted via the Internet to the physician's office for analysis—potentially eliminating unnecessary visits in some cases and encouraging immediate medical follow-up in others.

I. Methods of Monitoring Hip Implants

Figure 12:
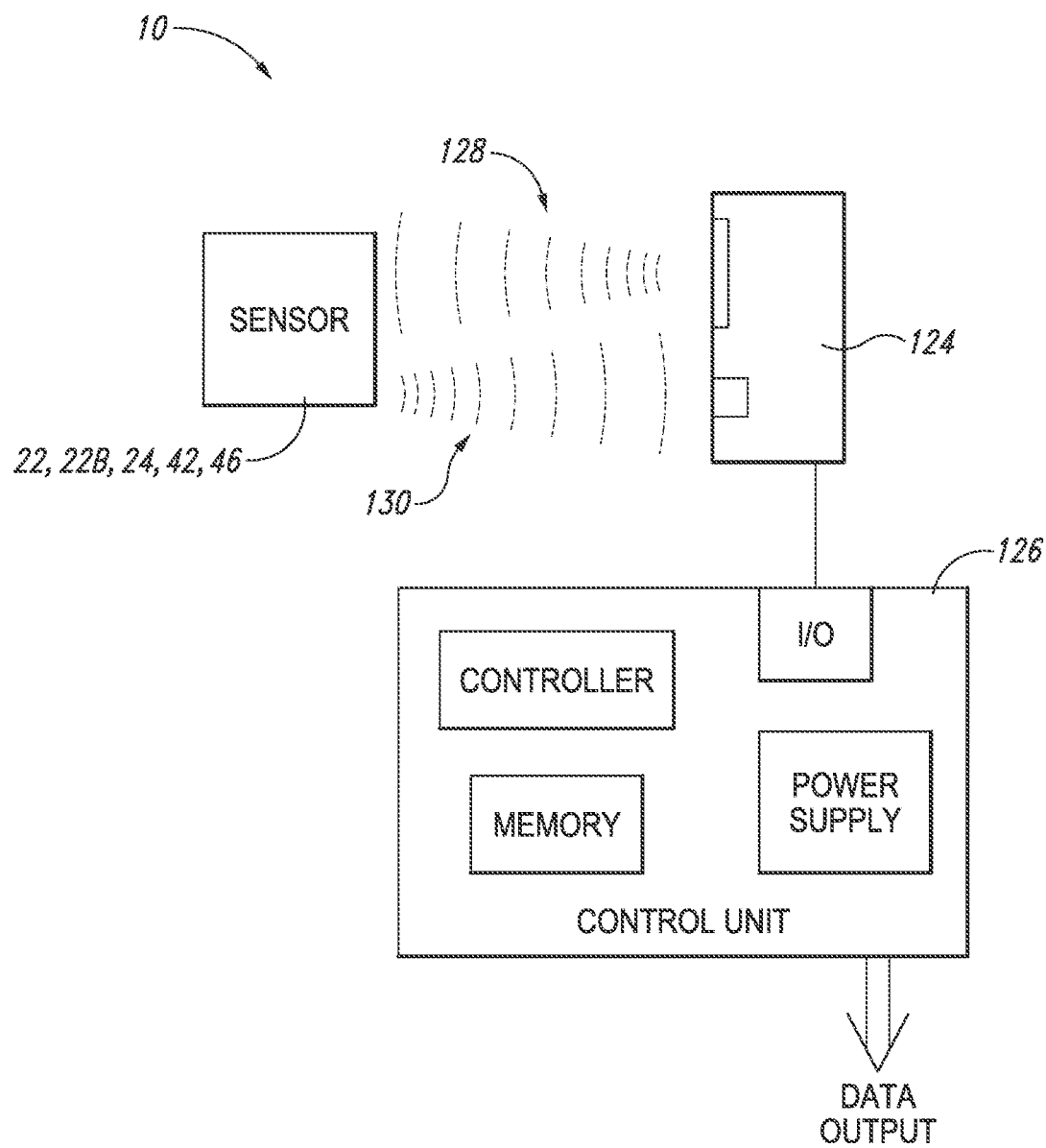
FIG. 12 illustrates an information and communication technology system embodiment arranged to process sensor data.

As noted above, the present invention also provides methods for monitoring one or more of the hip implants provided herein. For example, FIG. 12 illustrates a monitoring system usable with the hip implant 10 as of the type shown in any one of Figures described above. The monitoring system includes a sensor (e.g., 22, 22B, 24, 42 and/or 46) an interrogation module 124, and a control unit 126. The sensor (e.g., 22, 22B, 24, 42 and/or 46) is of the passive, wireless type which can operate on power received from a wireless source. Such sensors of this type are well known in the art and widely available. A pressure sensor of this type might be a MEMS pressure sensor, for example, Part No. LPS331AP, sold on the open market by STMicroelectronics. MEMS pressure sensors are well known to operate on very low power and suitable to remain unpowered and idle for long periods of time. They can be provided power wirelessly on an RF signal and, based on the power received wirelessly on the RF signal, perform the pressure sensing and then output the sensed data.

In one embodiment, an electrical generation system (as described above) is provided that can be utilized to power the sensors described herein. During operation, as shown in FIG. 12, an interrogation module 124 outputs a signal 128. The signal 128 is a wireless signal, usually in the RF band, that contains power for the sensor (e.g., 22, 22B, 24, 42 and/or 46) as well as an interrogation request that the sensors 22 perform a sensing. Upon being interrogated with the signal 128, the sensor (e.g., 22, 22B, 24, 42 and/or 46) powers up and stores power in onboard capacitors sufficient to maintain operation during the sensing and data reporting. Such power receiving circuits and storing on onboard capacitors are well known in the art and therefore need not be shown in detail. The appropriate sensing is carried out by the sensor (e.g., 22, 22B, 24, 42 and/or 46) and then the data is output from the sensor back to the interrogation module 124 on a signal 130, where it is received at an input port of the integration module.

According to one embodiment, sufficient signal strength is provided in the initial signal 128 to provide power for the sensor and to carry out the sensing operation and output the signal back to the interrogation module 124. In other embodiments, two or more signals 128 are sent, each signal providing additional power to the sensor to permit it to complete the sensing operation and then provide sufficient power to transfer the data via the signal path 130 back to the interrogation module 124. For example, the signal 128 can be sent continuously, with a sensing request component at the first part of the signal and then continued providing, either as a steady signal or pulses to provide power to operate the sensor. When the sensor is ready to output the data, it sends a signal alerting the interrogation module 124 that data is coming and the signal 128 can be turned off to avoid interference. Alternatively, the integration signal 128 can be at a first frequency and the output signal 130 at a second frequency separated sufficiently that they do not interfere with each other. In a preferred embodiment, they are both the same frequency so that the same antenna on the sensor can receive the signal 128 and send signal 130.

The interrogation signal 128 may contain data to select specific sensors on the hip replacement. For example, the signal 128 may power up all sensors on the hip replacement at the same time and then send requests for data from each at different selected times so that with one interrogation signal 128 provided for a set time, such as 1-2 seconds, results in each of the sensors on the hip replacement collecting data during this time period and then, at the end of the period, reporting the data out on respective signals 130 at different times over the next 0.5 to 2 seconds so that with one interrogation signal 128, the data from all sensors 22 is collected.

The interrogation module 124 is operating under control of the control unit 126 which has a microprocessor for the controller, a memory, an I/O circuit to interface with the interrogation module and a power supply. The control unit may output data to a computer or other device for display and use by the physician to treat the subject.

Figure 13:
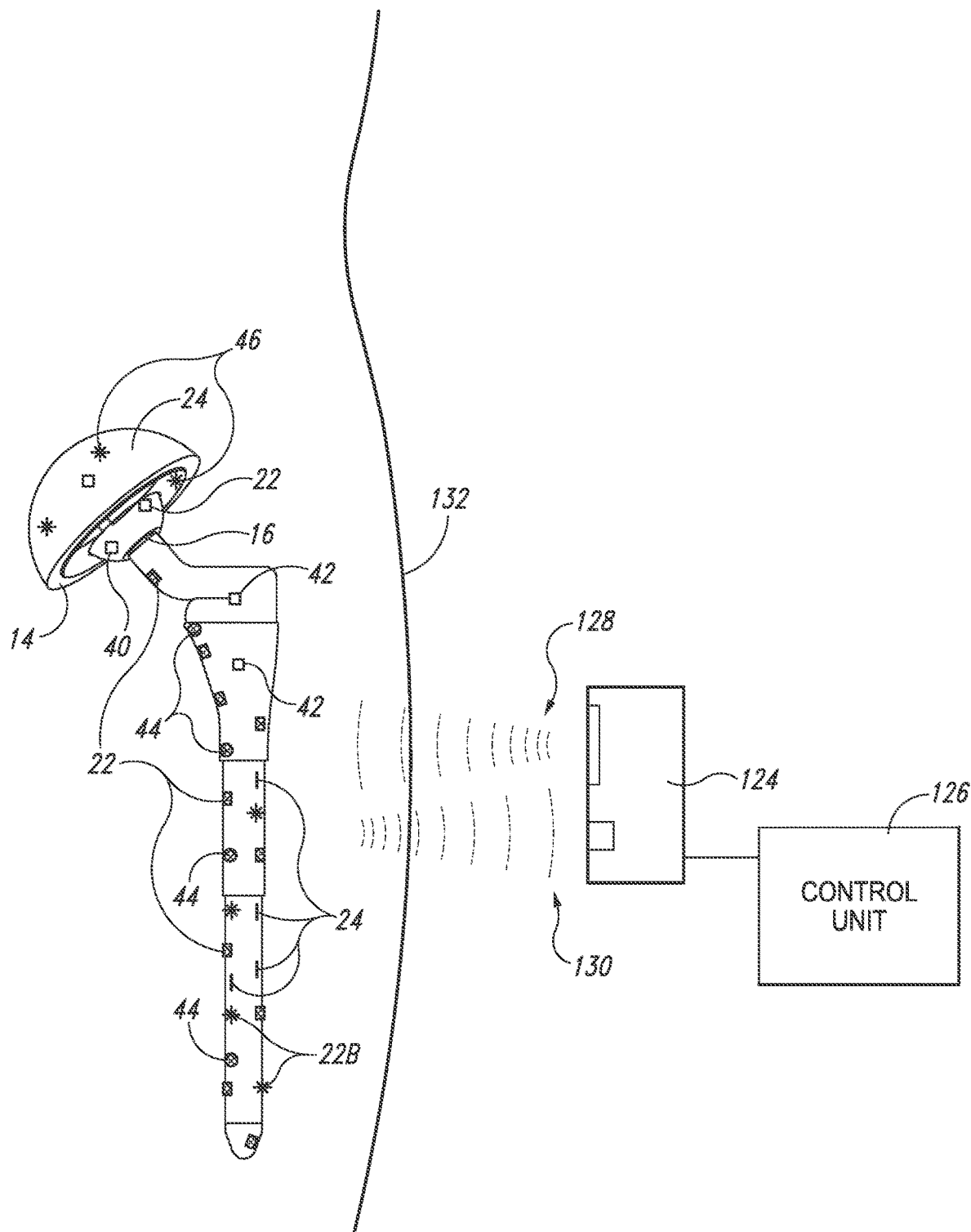
FIG. 13 is a block diagram of a sensor, interrogation module, and a control unit according to one embodiment of the invention.

FIG. 13 illustrates the operation according to a preferred embodiment within a subject. The subject has an outer skin 132. As illustrated in FIG. 13, the interrogation module 124 and control unit 126 are positioned outside the skin 132 of the subject. The interrogation signal 128 passes through the skin of the subject with a wireless RF signal, and the data is received on a wireless RF signal 130 from the sensor (e.g., 22, 22B, 24, 42 and/or 46) back to the interrogation module 124. While the wireless signal can be in any frequency range, an RF range is preferred. A frequency in the VLF to LF ranges of between 3-1300 kHz is preferred to permit the signal to be carried to sufficient depth inside the body with low power, but frequencies below 3 kHz and above 1300 kHz can also be used. The sensing does not require a transfer of large amounts of data and low power is preferred; therefore, a low frequency RF signal is acceptable. This also avoids competition from and inadvertent activation by other wireless signal generators, such as blue tooth, cell phones and the like.

Figure 14:
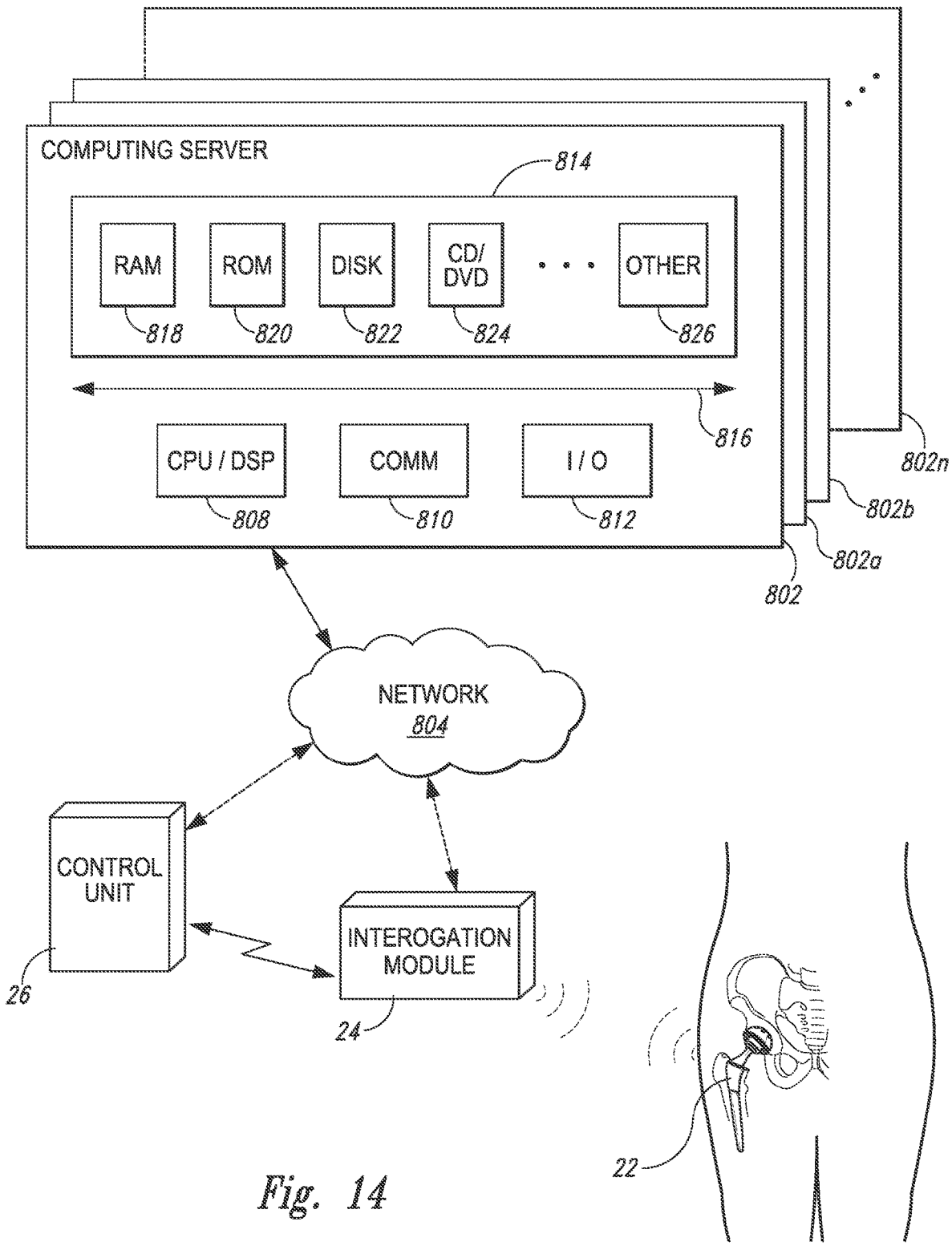
FIG. 14 is a schematic illustration of one or more sensors positioned on a hip replacement within a subject which is being probed for data and outputting data, according to one embodiment of the invention.

J. Collection, Transmission, Analysis, and Distribution of Data from Hip Implants FIG. 14 illustrates one embodiment of an information and communication technology (ICT) system 800 arranged to process sensor data (e.g., data from sensor (e.g., 22, 22B, 24, 42 and/or 46) of any one of Figures provided herein). In FIG. 14, the ICT system 800 is illustrated to include computing devices that communicate via a network 804, however in other embodiments, the computing devices can communicate directly with each other or through other intervening devices, and in some cases, the computing devices do not communicate at all. The computing devices of FIG. 14 include computing servers 802, control units 126, interrogation units 124, and other devices that are not shown for simplicity.

In FIG. 14, one or more sensors (e.g., 22, 22B, 24, 42 and/or 46) communicate with an interrogation module 124. The interrogation module 124 of FIG. 14 is directed by a control unit 126, but in other cases, interrogation modules 124 operates autonomously and passes information to and from sensors 22. One or both of the interrogation module 124 and control unit 126 can communicate with the computing server 802.

Within certain embodiments, the interrogation module and/or the control unit may be a wearable device on the subject. The wearable device (e.g., a watch-like device, a wrist-band, glasses or other device that may be carried or worn by the subject) can interrogate the sensors over a set (or random) period of time, collect the data, and forward the data on to one or more networks (804). Furthermore, the wearable device may collect data of its own accord which can also be transmitted to the network. Representative examples of data that may be collected include location (e.g., a GPS), body or skin temperature, and other physiologic data (e.g., pulse). Within yet other embodiments, the wearable device may notify the subject directly of any of a number of prescribed conditions, including but not limited to possible or actual failure of the device.

The information that is communicated between an interrogation module 124 and a sensor (e.g., 22, 22B, 24, 42 and/or 46) may be useful for many purposes as described herein. In some cases, for example, sensor data information is collected and analyzed expressly for the health of an individual subject. In other cases, sensor data is collected and transmitted to another computing device to be aggregated with other data (for example, the sensor data from 22 may be collected and aggregated with other data collected from a wearable device (e.g., a device that may, in certain embodiments, include GPS data and the like).

FIG. 14 illustrates aspects of a computing server 802 as a cooperative bank of servers further including computing servers 802a, 802b, and one or more other servers 802n. It is understood that computing server 802 may include any number of computing servers that operate individually or collectively to the benefit of users of the computing servers.

In some embodiments, the computing servers 802 are arranged as cloud computing devices created in one or more geographic locations, such as the United States and Canada. The cloud computing devices may be created as MICROSOFT AZURE cloud computing devices or as some other virtually accessible remote computing service.

An interrogation module 124 and a control unit 126 are optionally illustrated as communicating with a computing server 802. Via the interrogation module 124 or control unit 126, sensor data is transferred to (and in addition or alternatively from) a computing server 802 through network 804.

The network 804 includes some or all of cellular communication networks, conventional cable networks, satellite networks, fiber-optic networks, and the like configured as one or more local area networks, wide area networks, personal area networks, and any other type of computing network. In a preferred embodiment, the network 804 includes any communication hardware and software that cooperatively works to permit users of computing devices to view and interact with other computing devices.

Computing server 802 includes a central processing unit (CPU) digital signal processing unit (DSP) 808, communication modules 810, Input/Output (I/O) modules 812, and storage module 814. The components of computing server 802 are cooperatively coupled by one or more buses 816 that facilitate transmission and control of information in and through computing server 802. Communication modules 810 are configurable to pass information between the computer server 802 and other computing devices (e.g., computing servers 802a, 802b, 802n, control unit 126, interrogation unit 124, and the like). I/O modules 812 are configurable to accept input from devices such as keyboards, computer mice, trackballs, and the like. I/O modules 812 are configurable to provide output to devices such as displays, recorders, LEDs, audio devices, and the like.

Storage module 814 may include one or more types of storage media. For example, storage module 814 of FIG. 14 includes random access memory (RAM) 818, read only memory (ROM) 810, disk based memory 822, optical based memory 8124, and other types of memory storage media 8126. In some embodiments one or more memory devices of the storage module 814 has configured thereon one or more database structures. The database structures may be used to store data collected from sensors 22.

In some embodiments, the storage module 814 may further include one or more portions of memory organized a non-transitory computer-readable media (CRM). The CRM is configured to store computing instructions executable by a CPU 808. The computing instructions may be stored as one or more files, and each file may include one or more computer programs. A computer program can be standalone program or part of a larger computer program. Alternatively or in addition, each file may include data or other computational support material for an application that directs the collection, analysis, processing, and/or distribution of data from sensors (e.g., hip replacement sensors). The sensor data application typically executes a set of instructions stored on computer-readable media.

It will be appreciated that the computing servers shown in the figures and described herein are merely illustrative and are not intended to limit the scope of the present invention. Computing server 802 may be connected to other devices that are not illustrated, including through one or more networks such as the Internet or via the Web that are incorporated into network 804. More generally, a computing system or device (e.g., a "client" or "server") or any part thereof may comprise any combination of hardware that can interact and perform the described types of functionality, optionally when programmed or otherwise configured with software, including without limitation desktop or other computers, database servers, network storage devices and other network devices, PDAs, cell phones, wireless phones, pagers, electronic organizers, Internet appliances, television-based systems (e.g., using set-top boxes and/or personal/digital video recorders), and various other products that include appropriate inter-communication capabilities. In addition, the functionality provided by the illustrated system modules may in some embodiments be combined in fewer modules or distributed in additional modules. Similarly, in some embodiments the functionality of some of the illustrated modules may not be provided and/or other additional functionality may be available.

In addition, while various items are illustrated as being stored in memory or on storage while being used, these items or portions of them can be transferred between memory and other storage devices for purposes of memory management and/or data integrity. In at least some embodiments, the illustrated modules and/or systems are software modules/systems that include software instructions which, when executed by the CPU/DSP 808 or other processor, will program the processor to automatically perform the described operations for a module/system. Alternatively, in other embodiments, some or all of the software modules and/or systems may execute in memory on another device and communicate with the illustrated computing system/device via inter-computer communication.

Furthermore, in some embodiments, some or all of the modules and/or systems may be implemented or provided in other manners, such as at least partially in firmware and/or hardware means, including, but not limited to, one or more application-specific integrated circuits (ASICs), standard integrated circuits, controllers (e.g., by executing appropriate instructions, and including microcontrollers and/or embedded controllers), field-programmable gate arrays (FPGAs), complex programmable logic devices (CPLDs), and the like. Some or all of the systems, modules, or data structures may also be stored (e.g., as software instructions or structured data) on a transitory or non-transitory computer-readable storage medium 814, such as a hard disk 822 or flash drive or other non-volatile storage device 8126, volatile 818 or non-volatile memory 810, a network storage device, or a portable media article (e.g., a DVD disk, a CD disk, an optical disk, a flash memory device, etc.) to be read by an appropriate input or output system or via an appropriate connection. The systems, modules, and data structures may also in some embodiments be transmitted as generated data signals (e.g., as part of a carrier wave or other analog or digital propagated signal) on a variety of computer readable transmission mediums, including wireless-based and wired/cable-based mediums. The data signals can take a variety of forms such as part of a single or multiplexed analog signal, as multiple discrete digital packets or frames, as a discrete or streaming set of digital bits, or in some other form. Such computer program products may also take other forms in other embodiments. Accordingly, the present invention may be practiced with other computer system configurations.

In FIG. 14, sensor data from, e.g., sensor (e.g., 22, 22B, 24, 42 and/or 46) is provided to computing server 802. Generally speaking, the sensor data, represents data retrieved from a known subject and from a known sensor. The sensor data may possess include or be further associated with additional information such as the USI, UDI, a time stamp, a location (e.g., GPS) stamp, a date stamp, and other information. The differences between various sensors is that some may include more or fewer data bits that associate the data with a particular source, collection device, transmission characteristic, or the like.

In some embodiments, the sensor data may comprise sensitive information such as private health information associated with a specific subject. Sensitive information, for example sensor data from sensor (e.g., 22, 22B, 24, 42 and/or 46), may include any information that an associated party desires to keep from wide or easy dissemination. Sensitive information can stand alone or be combined with other non-sensitive information. For example, a subject's medical information is typically sensitive information. In some cases, the storage and transmission of a subject's medical information is protected by a government directive (e.g., law, regulation, etc.) such as the U.S. Health Insurance Portability and Accountability Act (HIPPA).

As discussed herein, a reference to "sensitive" information includes information that is entirely sensitive and information that is some combination of sensitive and non-sensitive information. The sensitive information may be represented in a data file or in some other format. As used herein, a data file that includes a subject's medical information may be referred to as "sensitive information." Other information, such as employment information, financial information, identity information, and many other types of information may also be considered sensitive information.

A computing system can represent sensitive information with an encoding algorithm (e.g., ASCII), a well-recognized file format (e.g., PDF), or by some other format. In a computing system, sensitive information can be protected from wide or easy dissemination with an encryption algorithm.

Generally speaking, sensitive information can be stored by a computing system as a discrete set of data bits. The set of data bits may be called "plaintext." Furthermore, a computing system can use an encryption process to transform plaintext using an encryption algorithm (i.e., a cipher) into a set of data bits having a highly unreadable state (i.e., cipher text). A computing system having knowledge of the encryption key used to create the cipher text can restore the information to a plaintext readable state. Accordingly, in some cases, sensitive data (e.g., sensor data 806a, 806b) is optionally encrypted before being communicated to a computing device.

In one embodiment, the operation of the information and communication technology (ICT) system 800 of FIG. 14 includes one or more sensor data computer programs stored on a computer-readable medium. The computer program may optionally direct and/or receive data from one or more hip replacement sensors implanted in one or more subjects. A sensor data computer program may be executed in a computing server 802. Alternatively, or in addition, a sensor data computer program may be executed in a control unit 126, an interrogation unit 124.

In one embodiment, a computer program to direct the collection and use of hip replacement sensor data is stored on a non-transitory computer-readable medium in storage module 814. The computer program is configured to identify a subject who has a wireless hip replacement inserted in his or her body. The wireless hip replacement may include one or more wireless sensor In some cases, the computer program identifies one subject, and in other cases, two or more subjects are identified. The subjects may each have one or more wireless hip replacements, and each wireless hip replacement may have one or more wireless sensors of the type described herein.

The computer program is arranged to direct the collection of sensor data from the wireless hip replacement devices. The sensor data is generally collected with a wireless interrogation unit 124. In some cases, the program communicates with the wireless interrogation unit 124. In other cases, the program communicates with a control unit 126, which in turn directs a wireless interrogation unit 124. In still other cases, some other mechanism is used direct the collection of the sensor data.

Once the sensor data is collected, the data may be further processed. For example, in some cases, the sensor data includes sensitive subject data, which can be removed or disassociated with the data. The sensor data can be individually stored (e.g., by unique sensor identification number, device number, etc.) or aggregated together with other sensor data by sensor type, time stamp, location stamp, date stamp, subject type, other subject characteristics, or by some other means.

The following pseudo-code description is used to generally illustrate one exemplary algorithm executed by a computing server 802 and generally described herein with respect to FIG. 14:

```
Start
   Open a secure socket layer (SSL)
   Identify a subject
   Communicate with a predetermined control unit
   Request sensor data from the subject via the control unit
   Receive sensor data
   If the sensor data is encrypted
      THEN decrypt the sensor data
   Store encrypted data in the selected storage locations
   Aggregate the sensor data with other sensor data
   Store encrypted data in the selected storage locations
   Maintain a record of the storage transaction
   Perform post storage actions
End
```

Those skilled in the art will recognize that it is common within the art to implement devices and/or processes and/or systems, and thereafter use engineering and/or other practices to integrate such implemented devices and/or processes and/or systems into more comprehensive devices and/or processes and/or systems. That is, at least a portion of the devices and/or processes and/or systems described herein can be integrated into other devices and/or processes and/or systems via a reasonable amount of experimentation. Those having skill in the art will recognize that examples of such other devices and/or processes and/or systems might include—as appropriate to context and application—all or part of devices and/or processes and/or systems of (a) an air conveyance (e.g., an airplane, rocket, helicopter, etc.), (b) a ground conveyance (e.g., a car, truck, locomotive, tank, armored personnel carrier, etc.), (c) a building (e.g., a home, warehouse, office, etc.), (d) an appliance (e.g., a refrigerator, a washing machine, a dryer, etc.), (e) a communications system (e.g., a networked system, a telephone system, a Voice over IP system, etc.), (f) a business entity (e.g., an Internet Service Provider (ISP) entity such as Comcast Cable, Qwest, Southwestern Bell, etc.), or (g) a wired/ wireless services entity (e.g., Sprint, Cingular, Nextel, etc.), etc.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory).

A sale of a system or method may likewise occur in a territory even if components of the system or method are located and/or used outside the territory. Further, implementation of at least part of a system for performing a method in one territory does not preclude use of the system in another territory.

In conclusion, hip replacements utilizing a variety of sensors can be utilized to serve a variety of critical clinical functions, such as safe, accurate and less traumatic placement and deployment of the hip replacement, procedural and post-operative "real time" imaging of hip replacement and the surrounding anatomy, the development of hip replacement complications, and the patient's overall health status. Currently, post-operative (both in hospital and out-patient) evaluation of hip replacement patients is through patient history, physical examination and medical monitoring that is supplemented with diagnostic imaging studies as required. However, most of the patient's recuperative period occurs between hospital and office visits and the majority of data on daily function goes uncaptured; furthermore, monitoring patient progress through the use of some diagnostic imaging technology can be expensive, invasive and carry its own health risks (coronary angiography for example). It can, therefore, be very difficult to accurately measure and follow the development or worsening of symptoms and evaluate "real life" hip replacement performance, particularly as they relate to patient activity levels, exercise tolerance, and the effectiveness of rehabilitation efforts and medications.

At present, neither the physician nor the patient has access to the type of "real time," continuous, objective, hip replacement performance measurements that they might otherwise like to have. Being able to monitor in situ hip replacement function, integrity, anatomy and physiology can provide the physician with valuable objective information during office visits; furthermore, the patient can take additional readings at home at various times (e.g. when experiencing pain, during exercise, after taking medications, etc.) to provide important complementary clinical information to the doctor (which can be sent to the healthcare provider electronically even from remote locations). From the perspective of the patient, being able to monitor many of these same parameters at home allows them to take a more proactive role in their care and recovery and provide him or her with either an early warning indicator to seek medical assistance or with reassurance.

In one alternative, the patient may have a reading device in their home which collates the data from the hip replacement on a periodic basis, such as once per day or once per week. In addition to empowering the patient to follow their own rehabilitation—and enabling them to see the positive (and negative) effects of various lifestyle choices on their health and rehabilitation—such information access can be expected to improve compliance and improve patient outcomes. For example, within certain embodiments the devices and systems provided herein can instruct or otherwise notify the patient, or a permitted third-party as to deviations (e.g., greater than 10%, 20%, 25%, 50%, 70%, and or 100%) from normal, and/or, set parameters. Furthermore, their recovery experience can be shared via the web with other patients to compare their progress versus expected "norms" for function and rehabilitation and alert them to signs and symptoms that should be brought to their doctor's attention. From a public health perspective, the performance of different hip replacements can be compared in different patients (different sexes, disease severity, activity levels, concurrent diseases such as hypertension and diabetes, smoking status, obesity, etc.) to help manufacturers design better hip replacements and assist physicians in the selection of the right hip replacement for a specific patient types. Payers, patients, manufacturers and physicians could all benefit from the collection of this comparative information. Poor and dangerous products could be identified and removed from the market and objective long-term effectiveness data collected and analyzed. Lastly, data accumulated at home can be collected and transmitted via the Internet to the physician's office for analysis—potentially eliminating unnecessary visits in some cases and encouraging immediate medical follow-up in others.

The following are some specific numbered embodiments of the systems and processes disclosed herein. These embodiments are exemplary only. It will be understood that the invention is not limited to the embodiments set forth herein for illustration, but embraces all such forms thereof as come within the scope of the above disclosure.

1) A hip replacement prosthesis comprising:
a femoral stem;
a femoral head coupled to the femoral stem;
an acetabular assembly coupled to the femoral head; and
a plurality of sensors coupled to at least one of the femoral stem, femoral head and the acetabular assembly.

2) The hip replacement prosthesis of embodiment 1 wherein the plurality of sensors includes a sensor on the femoral stem.

3) The hip replacement prosthesis of embodiment 1 wherein the plurality of sensors includes a sensor on the femoral head.

4) The hip replacement prosthesis of embodiment 1 wherein the plurality of sensors includes a sensor on the acetabular assembly.

5) The hip replacement prosthesis according to any one of embodiments 1 to 4 wherein said sensor is selected from the group consisting of accelerometers, pressure sensors, contact sensors, position sensors, chemical microsensors, tissue metabolic sensors, mechanical stress sensors and temperature sensors.

6) The hip replacement prosthesis according to embodiment 5 wherein said accelerometer detects acceleration, tilt, vibration, shock and or rotation.

7) The hip replacement prosthesis of embodiment 1 wherein the plurality of sensors includes contact sensors positioned between the femoral head and the acetabular assembly.

8) The hip replacement prosthesis of embodiment 1 wherein the plurality of sensors includes a plurality of contact sensors positioned on the outer surface of the acetabular assembly.

9) The hip replacement prosthesis of embodiment 1 wherein the plurality of sensors includes a plurality of contact sensors positioned on the outer surface of the acetabular assembly.

10) The hip replacement prosthesis of embodiment 1 wherein the plurality of sensors includes a plurality of strain sensors positioned between the femoral head the acetabular assembly.

11) The hip replacement prosthesis of embodiment 1 wherein the plurality of sensors includes accelerometers positioned on the femoral stem.

12) The hip replacement prosthesis of embodiment 1 wherein the acetabular assembly includes an acetabular shell and an acetabular liner.

13) The hip replacement prosthesis of embodiment 7 further including strain sensors positioned between the acetabular liner and the acetabular shell.

14) A medical device, comprising a femoral stem and a plurality of sensors coupled to said femoral stem.

15) A medical device, comprising a femoral head and a plurality of sensors coupled to said femoral head.

16) A medical device, comprising an acetabular assembly and a plurality of sensors coupled to said acetabular assembly.

17) The medical device according to any one of embodiments 14 to 16, wherein said sensors are placed within and on the surface of said medical device.

18) The medical device according to any one of embodiments 14 to 17 wherein said sensor is selected from the group consisting of accelerometers, pressure sensors, contact sensors, position sensors, chemical microsensors, tissue metabolic sensors, mechanical stress sensors and temperature sensors.

19) The medical device according to embodiment 18 wherein said accelerometer detects acceleration, tilt, vibration, shock and or rotation.

20) The hip replacement prosthesis or medical device according to any one of embodiments 1 to 19, further including:
an electronic processor positioned inside the femoral stem that is electrically coupled to sensors.

21) The hip replacement prosthesis or medical device according to embodiment 20 wherein the electric coupling is a wireless coupling.

22) The hip replacement prosthesis or medical device according to embodiments 20 or 21 further including:
a memory coupled to the electronic processor and positioned inside the femoral stem.

23) The hip replacement or medical device according to any one of embodiments 1 to 22 wherein said sensor is a plurality of sensors which are positioned on or within said hip replacement prosthesis or medical device at a density of greater than 1, 2, 3, 4, 5, 6, 7, 8, 9, 10 or 20 sensors per square centimeter.

24) The hip replacement prosthesis or medical device according to any one of embodiments 1 to 22 wherein said sensor is a plurality of sensors which are positioned on or within said hip replacement at a density of greater than 1, 2, 3, 4, 5, 6, 7, 8, 9, 10 or 20 sensors per cubic centimeter.

25) A method comprising:
obtaining contact data from contact sensors positioned at a plurality of locations between a femoral head and an acetabular assembly located in-situ in the hip of a patient;
storing the data in a memory located in a femoral stem that is coupled to the femoral head; and
transferring the data from the memory to a location outside the femoral stem.

26) The method according to embodiment 25 further including:
obtaining strain data from strain sensors positioned at a plurality of locations between the femoral head and the acetabular assembly located in-situ in the hip of a patient;
storing the strain data in a memory located in the femoral stem that is coupled to the femoral head; and
transferring the strain data from the memory in the femoral stem to a memory in location outside the femoral stem.

27) The method according to embodiment 25 further including:
obtaining contact data from contact sensors positioned between the acetabular assembly and a pelvis bone of a patient while in-situ in the patient;
storing the contact data in a memory located in the femoral stem; and
transferring the data from the memory in the femoral stem to a memory in a location outside of the femoral stem.

28) A method comprising:
obtaining acceleration data from accelerometers positioned at a plurality of locations on a hip replacement assembly located in-situ in the hip of a patient;
storing the acceleration data in a memory located in a femoral stem that is coupled to the femoral head; and
transferring the acceleration data from the memory in the femoral stem to a memory in a location outside the femoral stem.

29) A method comprising a) obtaining data from a sensor from a hip replacement prosthesis or medical device according to any one of embodiments 1 to 24; b) storing the data in memory at a storage site within a hip replacement prosthesis or medical device according to any one of embodiments 1 to 24; and c) transferring the data from the memory to a location outside of the storage site.

30) The method according to embodiment 29, wherein said hip replacement prosthesis or medical device is implanted within a subject, and the data is transferred to a site outside of the subject.

31) The method according to embodiment 30 wherein said data is transferred to a watch, wrist band, cell phone or glasses.

32) The method according to embodiment 30 wherein said data is transferred to a residence or an office.

33) The method according to embodiment 30 wherein said data is transferred to a health care provider.

34) The method according to any one of embodiments 25 to 33, further comprising the step of analyzing the data.

35) A non-transitory computer-readable storage medium whose stored contents configure a computing system to perform a method, the method comprising:
identifying a subject, the identified subject having at least one wireless hip implant, said hip implant having one or more sensors;
detecting a wireless interrogation unit to collect sensor data from at least one of the respective sensors; and
receiving the collected sensor data.

36) The storage medium according to embodiment 35 whose stored contents configure a computing system to perform a method, the method further comprising:
removing sensitive subject data from the collected sensor data; and parsing the data according to the type or location of sensor.

37) The storage medium according to embodiment 35 or 36 wherein said hip implant is a hip replacement prosthesis or medical device according to any one of embodiments 1 to 24.

38) The storage medium according to any one of embodiments 35 to 37 wherein said data is received on a watch, wrist band, cell phone or glasses.

39) The storage medium according to any one of embodiments 35 to 38 wherein said data is received within a subject's residence or office.

40) The storage medium according to any one of embodiments 35 to 39 wherein said data is provided to a health care provider.

41) The storage medium according to any one of embodiments 35 to 40 wherein said data is posted to one or more websites.

42) A method according to any one of embodiments 25 to 34 or storage medium according to any one of embodiments 35 to 41, wherein said data is plotted to enable visualization of change over time.

43) The method or storage medium according to embodiment 42 wherein said data is plotted to provide a two or three-dimensional image.

44) The method or storage medium according to embodiment 42 or 43 wherein said data is plotted to provide a moving two or three dimensional image.

45) The method or storage medium according to anyone of embodiments 42 to 44, wherein said data is utilized to determine the range of motion of a subject with a hip implant prosthesis or medical device.

46) The method or storage medium according to anyone of embodiments 42 to 44, wherein said data is utilized to determine or predict any deficiencies or malfunctions of the hip implant prosthesis or medical device.

47) A method for detecting degradation in a hip replacement prosthesis or medical device, comprising the steps of a) providing to a subject a hip implant prosthesis or medical device according to any one of embodiments 1 to 24; and b) detecting a change in a sensor, and thus determining degradation of the hip implant prosthesis or medical device.

48) The method according to embodiment 47 wherein said sensor is capable of detecting one or more physiological and or locational parameters.

49) A method for detecting an infection in a hip replacement prosthesis or medical device, comprising the steps of a) a) providing to a subject a hip implant prosthesis or medical device according to any one of embodiments 1 to 24; and b) detecting a change in a sensor, and thus determining infection of the hip implant prosthesis or medical device.

50) The method according to embodiment 49 wherein said change in a sensor is a rise in temperature.

51) A method for imaging a hip replacement prosthesis or medical device, comprising detecting the changes in sensors in, on, and or within a hip implant prosthesis or medical device according to anyone of embodiments 1 to 24, and wherein the hip implant prosthesis or medical device comprises sensors at a density of greater than 1, 2, 3, 4, 5, 6, 7, 8, 9, 10 or 20 sensors per square centimeter.

52) A method for imaging a hip implant prosthesis or medical device, comprising detecting changes in sensors in, on, and or within a hip implant prosthesis or medical device according to any one of embodiments 1 to 24 over time, and wherein the hip implant prosthesis or medical device comprises sensors at a density of greater than 1, 2, 3, 4, 5, 6, 7, 8, 9, 10 or 20 sensors per cubic centimeter.

53) The method according to embodiments 51 or 52, wherein said sensor is one or more of a fluid pressure sensor, contact sensor, position sensor, accelerometer, pressure sensor, blood volume sensor, blood flow sensor, blood chemistry sensor, blood metabolic sensor, mechanical stress sensor, a temperature sensor.

54) A method for placing a hip implant prosthesis or medical device within a subject, comprising a) implanting a hip implant prosthesis or medical device according to any one of embodiments 1 to 24, and b) detecting placement of the hip implant prosthesis or medical device by detecting a sensor.

55) The method according to embodiment 54 wherein the hip implant prosthesis or medical device comprises two or more sections, and wherein detection of said two or more sections can be determined by analysis of one or more sensors.

56) The method according to embodiments 54 or 55 wherein placement of the hip implant prosthesis or medical device can be visualized by a two or three dimensional representation or image of the one or more sensors on said hip implant prosthesis or medical device.

57) The method according to any one of embodiments 54 to 56, wherein said detecting placement of the hip implant prosthesis or medical device allows determination of whether the hip implant prosthesis or medical device is placed incorrectly.

Any of the various embodiments described above can be combined to provide further embodiments. All of the U.S. patents, U.S. patent application publications, U.S. patent applications, PCT application publications, foreign patents, foreign patent applications and non-patent publications referred to in this specification, are incorporated herein by reference, in their entirety. Aspects of the embodiments can be modified, if necessary to employ concepts of the various patents, applications and publications to provide yet further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A hip replacement prosthesis comprising:
a femoral assembly comprising a femoral head having an opening and a femoral implant, the femoral implant comprising a femoral neck and a femoral shaft, where the femoral head and the femoral implant are separate pieces that are assembled together by a coupling of the femoral neck into the opening of the femoral head to form the femoral assembly;
a plurality of sensors coupled to the femoral shaft;
at least one head/neck sensor pair comprising a first contact sensor associated with the femoral head and a second contact sensor associated with the femoral neck and positioned within the opening of the femoral head and adjacent the first contact sensor associated with the femoral head, wherein the at least one head/neck sensor pair is configured to detect contact between the femoral neck and the femoral head;
a two-piece acetabular component comprising an acetabular shell having an opening and an inner acetabular liner attached to the acetabular shell and configured to at least partially fit within the opening of the acetabular shell; and at least one shell/liner sensor pair comprising a first contact sensor associated with the acetabular shell and a second contact sensor associated with the inner acetabular liner and positioned within the opening of the acetabular shell and adjacent the first contact sensor associated with the acetabular shell, wherein the at least one shell/liner sensor pair is configured to detect contact between the acetabular shell and the inner acetabular liner.

2. The hip replacement prosthesis of claim 1 wherein the femoral neck and the femoral shaft are separate pieces that are assembled together to form the femoral implant.

3. The hip replacement prosthesis of claim 1 wherein the plurality of sensors comprises a plurality of accelerometers that measure acceleration.

4. The hip replacement prosthesis of claim 3 wherein the accelerometers are MEMS sensors.

5. The hip replacement prosthesis of claim 3 further comprising a gyroscope.

6. The hip replacement prosthesis of claim 1 wherein the plurality of sensors are either positioned on the femoral shaft or are contained within the femoral shaft.

7. The hip replacement prosthesis of claim 6 wherein the plurality of sensors are contained within the femoral shaft and are not positioned on the femoral shaft.

8. The hip replacement prosthesis of claim 7 wherein the plurality of sensors are contained within the femoral shaft at a density of greater than 5 sensors per cubic centimeter.

9. The hip replacement prosthesis according to claim 7 wherein each of the plurality of sensors contains a signal-receiving circuit and a signal-output circuit.

10. The hip replacement prosthesis of claim 7 wherein the femoral shaft additionally contains one or more of a processor circuit, CPU and memory chip.

11. The hip replacement prosthesis of claim 7 wherein the femoral shaft additionally contains an antenna for sending and receiving data measured by the plurality of sensors.

12. The hip replacement prosthesis of claim 7 further including an electronic processor positioned inside the femoral shaft that is electrically coupled to the plurality of sensors.

13. The hip replacement prosthesis of claim 12 wherein the electric coupling is a wireless coupling.

14. The hip replacement prosthesis of claim 12 further including a memory coupled to the electronic processor and contained within the femoral shaft, where the memory stores data collected by the plurality of sensors.

15. The hip replacement prosthesis according to claim 7 further comprising a power generator which provides power to the sensors.

16. The hip replacement prosthesis of claim 15 wherein a wire runs from the power generator to the sensors, where the wire can transfer the power to the sensors.

17. The hip replacement prosthesis of claim 7 wherein the plurality of sensors comprise a plurality of accelerometers that each measure acceleration.

18. The hip replacement prosthesis of claim 1 further comprising a strain sensor associated with one of the femoral head and the femoral neck, the strain sensor configured and arranged to sense strain between the femoral head and the femoral neck.

19. The hip replacement prosthesis of claim 1 further comprising a strain sensor associated with one of the acetabular shell and the inner acetabular liner, the strain sensor configured and arranged to sense strain between the acetabular shell and the inner acetabular liner.

20. The hip replacement prosthesis of claim 1 further comprising a strain sensor associated with one of the femoral head and the inner acetabular liner, the strain sensor configured and arranged to sense strain between the femoral head and the inner acetabular liner.

21. The hip replacement prosthesis of claim 1 further comprising at least one surface wear sensor corresponding to a contact pressure sensor at a depth beneath a surface of one of the femoral head and the inner acetabular liner.

22. The hip replacement prosthesis of claim 21 comprising a plurality of surface wear sensors, each corresponding to a contact pressure sensor, each surface wear sensor embedded beneath the surface at a different depth.

23. The hip replacement prosthesis of claim 1, wherein the femoral shaft has an opening and the plurality of sensors are mechanically attached to the femoral shaft by way of the opening to provide permanent attachment of the plurality of sensors to the femoral shaft.

24. The hip replacement prosthesis of claim 23, wherein the plurality of sensors comprises three accelerometers arranged to fit within a space of one square centimeter.

25. The hip replacement prosthesis of claim 24, wherein the plurality of accelerometers are arranged to provide data on range of motion of the femoral shaft.

* * * * *